United States Patent [19]

Musser et al.

[11] Patent Number: 5,212,182

[45] Date of Patent: May 18, 1993

[54] SUBSTITUTED QUINOLINYL- AND NAPHTHALENYLBENZAMIDES OR BENZYLAMINES AND RELATED COMPOUNDS USEFUL AS ANALGESICS

[75] Inventors: John H. Musser, Yardley, Pa.; Albert J. Molinari, Kingston; Dominick Mobilio, Franklin Park, both of N.J.

[73] Assignee: American Home Products Corpooration, New York, N.Y.

[21] Appl. No.: 592,160

[22] Filed: Oct. 3, 1990

[51] Int. Cl.⁵ .................... A61K 31/47; C07D 215/00
[52] U.S. Cl. ....................... 514/314; 514/311; 514/312; 514/313; 514/319; 546/152; 546/176; 546/177; 546/205; 546/206
[58] Field of Search ............... 546/152, 153, 157, 162, 546/168, 169, 171, 175, 176, 177, 178, 180, 205, 206; 514/311, 312, 313, 314, 319

[56] References Cited

U.S. PATENT DOCUMENTS

| | | | |
|---|---|---|---|
| 3,875,165 | 4/1975 | Archibald et al. | 546/161 |
| 3,971,787 | 7/1976 | Archibald et al. | 546/161 |
| 4,167,567 | 9/1979 | McCall | 544/212 |
| 4,357,333 | 11/1982 | Archibald et al. | 546/161 |
| 4,550,172 | 10/1985 | Musser et al. | 546/206 |
| 4,839,369 | 6/1989 | Youssefyeh et al. | 514/314 |

*Primary Examiner*—C. Warren Ivy
*Assistant Examiner*—Celia Chang
*Attorney, Agent, or Firm*—Walter Patton

[57] ABSTRACT

This invention relates to novel quinolinyl- and naphthalenylbenzamides or benylamines and related disclosed compounds of the formula

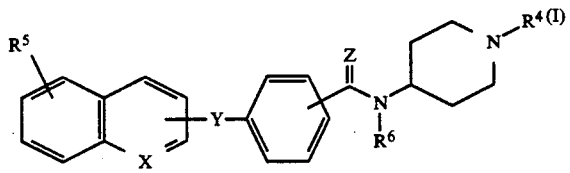

wherein X is nitrogen, NO or $CR^1$; Y is $C(R^1)(R^2)O$, $OC(R^1)(R^2)$, $C(R^1)(R^2)N(R^3)$, $N(R^3)C(R^1)(R^2)$ or $C(R^1)=C(R^2)$; wherein $R^1$, $R^2$, and $R^3$ are independently hydrogen or lower alkyl containing 1 to 10 carbon atoms; Z is oxygen or $(R^1)(R^2)$; $R^4$ is $R^1$, benzyl, benzyl ring substituted with $R^5$, benzyl alpha monosubstituted with $R^1$, benzyl ring substituted with $R^5$ and alpha monosubstituted with $R^1$, phenyl, phenylalkyl containing 2 to 10 carbon atoms in the alkyl group or phenylalkyl ring substituted with $R^5$ and containing 2 to 10 carbon atoms in the alkyl group; wherein $R^5$ is $R^1$, lower alkoxy containing 1 to 10 carbon atoms, halogen, trihalomethyl, $NO_2$, $N(R^1)(R^2)$ or $C(O)N(R^1)(R^2)$; $R^6$ is $R^1$ or $R^6$ is $C(O)(R^7)$ with the proviso that Z is not oxygen; and wherein $R^7$ is $R^1$, phenyl, perfluoroalkyl containing 1 to 10 carbon atoms, phenylalkyl containing 1 to 10 carbon atoms in the alkyl group; or a pharmaceutically acceptable acid addition salt thereof, and their use in the treatment of pain mediated by the biological peptide, bradykinin. In particular, the preferred compounds are where X is nitrogen, and Y is $CH_2O$ of the above structure.

1 Claim, No Drawings

SUBSTITUTED QUINOLINYL- AND NAPHTHALENYLBENZAMIDES OR BENZYLAMINES AND RELATED COMPOUNDS USEFUL AS ANALGESICS

This invention relates to novel quinolinyl- and naphthalenylbenzamides or benzylamines and related compounds possessing valuable pharmaceutical activity, particularly as bradykinin antagonists possessing analgesic properties.

BACKGROUND OF INVENTION

Bradykinin is known to produce intense pain when applied to the blister base in man, Kantor, et al., Proc. Soc. Exp. Biol. Med. 126: 505-507 (1967). In animals, its intraperitoneal injection induces writhing in rats and mice Collier, et al., Br. J. Pharmac. Chemoth. 32: 295-310 (1968); Dubinsky, et al., Prostaglandins 28(2): 241-252 (1984); and Loux, et al., Arzneim-Forsch Drug Res. 28(2): 1644-1647 (1978) and its intra-arterial injection causes pseudo affective responses in dogs and cats, Guzman, et al., Arch. Int. Pharmacodyn. 149 (3—3): 571-588 (1964); Juan, et al., Eur. J. Pharmaco. 65: 267-278 (1980); and Lim et al., Arch. Int. Pharmacodyn. 152(1-2): 25-58 (1964). The role of bradykinin in pain transmission is due in part to its direct effect on the pain receptors and in part to its indirect effect through the release of other mediators of pain and inflammation, Regoli, et al., Pharmacol. Rev. 32(1): 1-46 (1980). Essentially, most pain is associated, at least at the beginning, with inflammation at the peripheral receptor sites. Tissue injury causes the migration of polymorphonuclear leukocytes (PMN). Proteases released from PMN act on alpha 2-globulins to form bradykinin, which exerts both direct and indirect effects on pain transmission.

Bradykinin binds to the pain receptors at the nerve ending and causes the nerve to fire. The nerve impulses enter the spinal cord and cause the release of substance P which in turn amplifies the pain signals through an increase in nerve firing. Substance P also binds to the mast cells, stimulating histamine release, which causes further inflammation, thus enhancing the generation and propagation of pain impulses, Kantor, et al., Am. J. Med. 80 (S:3A): 3-9 (1986); and Shibata, et al., Jap. J. Pharmacol. 41: 427-429 (1986).

Bradykinin, at the same time, acts directly on the receptors of the capillary wall to increase the vascular permeability. Plasma exudation and increased leukocyte diapedesis follow. This allows inflammation to perpetuate and causes further release of mediators like prostaglandins, histamine and bradykinin, which all serve to further intensify the pain impulses, Yaksh, et al., in "Acetyl salicylic acid: New use for an old drug", ed. H. J. M. Barnett, J. Hirsh and J. F. Mustard, Raven Press, New York (1982) pp. 137-151.

Simultaneously bradykinin binds to mast cells, triggering the release of histamine, the ensuing additional inflammation and pain, and the cascade of reactions leading to the formation of more prostaglandins, Regoli, et al., Pharmacol. Rev. 32(1): 1-46 (1980). Thus, bradykinin, both by direct effects on cell membranes and indirect effects on the release of other mediators, triggers, transmits, and amplifies the pain impulses from the peripheral to the central sites. A bradykinin antagonist, therefore, would stop the pain signal before it reaches the central nervous system.

PRIOR ART

The closet methoxy-bridged prior art in U.S. Pat. No. 4,839,369 which discloses but does not claim alkyl piperazine derivatives as antiinflammatory and antiallergic agents. The compounds of the present invention are 4-aminopiperidines. The closest amino-bridged prior art are U.S. Pat. Nos. 3,875,165; 3,971,789; 4,357,333; and 4,167,567 which claim 4-quinolinylamino derivatives as antiinflammatory, antiallergic, antihypertensive, and analgesic agents. The compounds of the present invention are [(4-quinolinylmethyl)amino] derivatives.

SUMMARY OF THE INVENTION

The present invention is directed to substituted quinolinyl- and naphthalenylbenzamides or benzylamines and related compounds possessing bradykinin antagonist activity and exhibiting analgesic properties, characterized by Formula (I)

The compounds of the present invention are those of Formula (I)

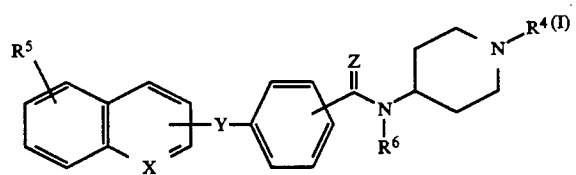

wherein X is nitrogen, NO or $CR^1$; Y is $C(R^1)(R^2)O$, $OC(R^1)(R^2)$, $C(R^1)(R^2)N(R^3)$, $N(R^3)C(R^1)(R^2)$ or $C(R^1)=C(R^2)$; wherein $R^1$, $R^2$, and $R^3$ are independently hydrogen or lower alkyl containing 1 to 10 carbon atoms; Z is oxygen or $(R^1)(R^2)$; $R^4$ is $R^1$, benzyl, benzyl ring substituted with $R^5$ benzyl alpha monosubstituted with $R^1$, benzyl ring substituted with $R^5$ and alpha monosubstituted with $R^1$, phenyl, phenylalkyl containing 2 to 10 carbon atoms in the alkyl group or phenylalkyl ring substituted with $R^5$ and containing 2 to 10 carbon atoms in the alkyl group; wherein $R^5$ is $R^1$, lower alkoxy containing 1 to 10 carbon atoms, halogen, trihalomethyl, $NO_2$, $N(R^1)(R^2)$ or $C(O)N(R^1)(R^2)$; $R^6$ is $R^1$ or $R^6$ is $C(O)(R^7)$ with the proviso that Z is not oxygen; and wherein $R^7$ is $R^1$, phenyl, perfluoroalkyl containing 1 to 10 carbon atoms, phenylalkyl containing 1 to 10 carbon atoms in the alkyl group or a pharmaceutically acceptable acid addition salt thereof.

Preferred compounds of the present invention are those of Formula (II)

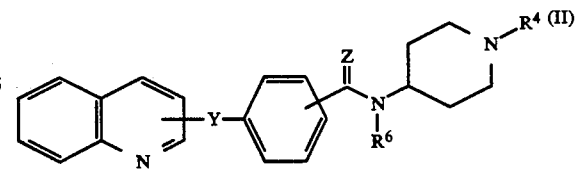

wherein Y is $C(R^1)(R^2)O$, $C(R^1)(R^2)N(R^3)$ or $C(R^1)=C(R^2)$; wherein $R^1$, $R^2$, and $R^3$ are independently hydrogen or lower alkyl containing 1 to 6 carbon atoms; Z is oxygen or $(R^1)(R^2)$; $R^4$ is $R^1$, benzyl, benzyl ring substituted with $R^5$, benzyl alpha monosubstituted with $R^1$, benzyl ring substituted with $R^5$ and alpha monosubstituted with $R^1$ or phenylalkyl containing 2 to 6 carbon atoms in the alkyl group; wherein $R^5$ is $R^1$ or $C(O)N(R^1)(R^2)$; $R^6$ is $R^1$ or $R^6$ is $C(O)(R^7)$ with the proviso that Z is not oxygen; and wherein $R^7$ is $R^1$, phenyl, phenylalkyl containing 1 to 6 carbon atoms in the alkyl group or a pharmaceutically acceptable acid addition salt thereof.

Further preferred compounds of the present invention are those of Formula (III)

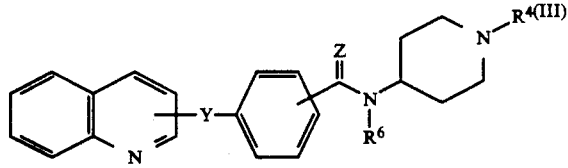

wherein Y is $CH_2O$, $CH_2NH$ or $CH=CH$ and further attached to the quinoline ring at positions 2 or 4; Z is oxygen or $H_2$; $R^4$ is benzyl or lower alkyl containing 1 to 6 carbon atoms; $R^6$ is hydrogen or $R^6$ is $C(O)(R^7)$ with the proviso that Z is $H_2$; and wherein $R^7$ is hydrogen, phenyl, lower alkyl containing 1 to 6 carbon atoms or a pharmaceutically acceptable acid addition salt thereof.

The present compounds can be prepared by procedures recognized in the art from known compounds or readily prepared intermediates. An exemplary general procedure (Scheme I) is as follows:

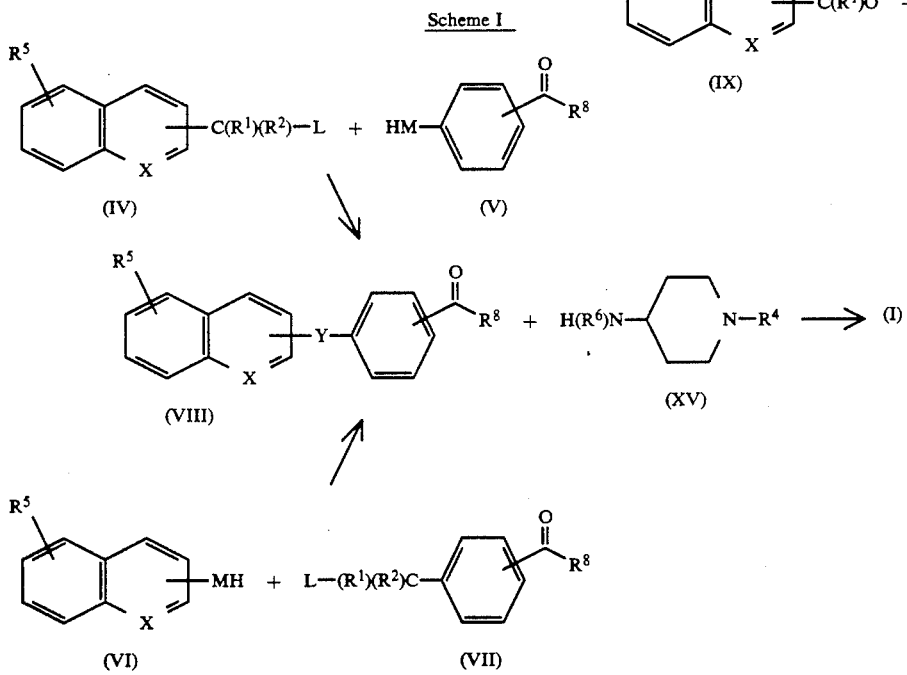

wherein Y, Z, $R^1$, $R^2$, $R^3$, $R^4$, and $R^5$ are defined as above; wherein further Y is not $CR^1=CR^2$; X is $CR^1$ or N; $R^6$ is $R^1$; $R^8$ is $R^1$ or $OR^1$, and L is a leaving group, such as hydroxy, halo, tosylate, or mesylate.

If M is oxygen and L is not hydroxy, any base normally employed to deprotonate an alcohol may be used, such as sodium hydride, potassium t-butoxide, sodium hydroxide, sodium alkoxide, Group Ia and IIa carbonates and bicarbonates, such as cesium carbonate and sodium bicarbonate, or tertiary amines, such as triethylamine or diisopropylethylamine. The above bases may also be used if M is $NR^3$.

If M is oxygen and L is hydroxy, reaction conditions such as diethylazodicarboxylate and triphenylphosphine in an inert solvent may be used, as well as dehydration conditions and dehydration conditions employing normally acidic reagents such as hydrogen halides, sulfonic or phosphoric acids, and the like.

Reaction temperature may range from $-20°$ C. to reflux and reaction times may vary from 0.25 hour to 72 hours. The reaction may be carried out in a solvent that is inert to all reactants. Solvents include, but are not limited to, N, N-dimethylformamide, dimethylsulfoxide, acetone, toluene, diethyl ether, diphenyl ether, tetrahydrofuran, dioxane, and the like, or, if appropriate, no solvent may be employed.

As a further variation (Scheme II), amino derivatives can be prepared by the condensation of an aldehyde or ketone of Formula (IX) with a primary amine of Formula (X), wherein X, $R^1$, $R^5$ and $R^8$ are defined hereinabove and $R^3$ is hydrogen, to form the corresponding imine. The imine is either reduced to give a compound of Formula (XI), wherein X, $R^1$, $R^5$, and $R^8$ are defined hereinabove and $R^2$ and $R^3$ are hydrogen, or alkylated with nucleophilic alkyl organometallic reagents, such as alkyl Scheme II

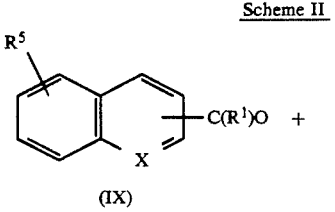

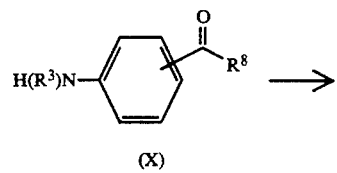

-continued
Scheme II

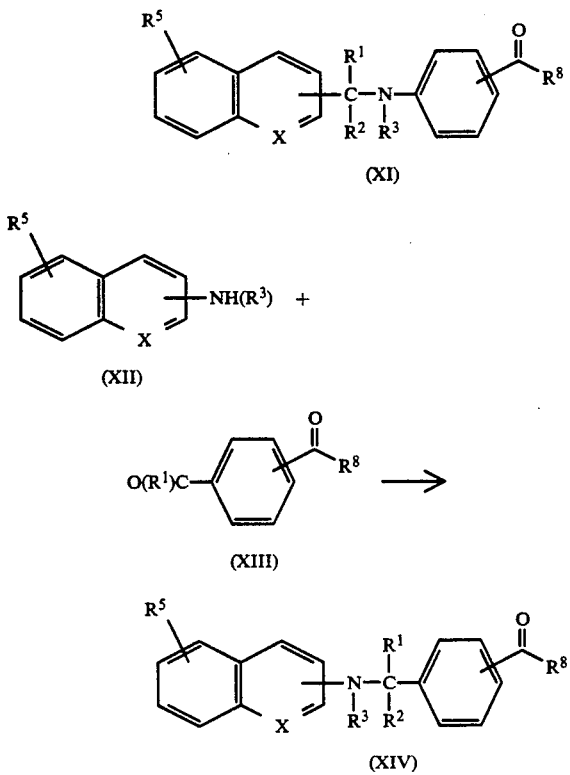

Grignard or alkyl lithium reagents, and the like to give a compound of Formula XI, wherein $R^2$ is lower alkyl, and $R^3$ is hydrogen.

Alternatively, amino derivatives can be prepared by the condensation of an aldehyde or ketone of Formula (XIII) with a primary amine of Formula (XII), wherein X, $R^1$, $R^5$, and $R^8$ are defined hereinabove and $R^3$ is hydrogen to form the corresponding imine. The imine is either reduced to give a compound of Formula (XIV), wherein X, $R^1$, $R^5$, and $R^8$ are defined hereinabove and $R^2$ and $R^3$ are hydrogen, or alkylated with nucleophilic alkyl organometallic reagents, such as alkyl Grignard or alkyl lithium reagents, and the like to give a compound of Formula (XIV), wherein $R^2$ is lower alkyl, and $R^3$ is hydrogen.

The product of either Formula (XI) or Formula (XIV), wherein $R^3$ is hydrogen, can be alkylated with alkylating agents known in the art, such as alkyl iodides, to form compounds of either Formula (XI) or Formula (XIV), wherein $R^3$ is lower alkyl.

The aforementioned condensation reaction to for the imines with subsequent reduction to the amines can be conveniently carried out in a single reaction step by mixing the aldehyde or ketone of either Formula (IX) or Formula (XIII) with the corresponding primary amine of Formula (X) or Formula (XII) under hydrogenation conditions. The aforesaid reactants can be hydrogenated over noble metal catalysts, such as platinum, palladium, rhodium, ruthenium, and the like, and the two stages occur under such conditions to produce the desired end products of Formula (XI) or Formula (XIV), wherein $R^3$ is hydrogen. Common hydrogenation solvents, such as methanol, ethanol, toluene, dichloromethane, chloroform, tetrahydrofuran, dioxane, diethyl ether, and the like may be employed at temperatures from room temperature to the reflux temperature of the reaction mixture.

Alternatively, the aforementioned condensation reaction to form the imines with subsequent reduction or alkylation to the amines can be conveniently carried out in two reaction steps by mixing the aldehyde or ketone of either Formula (IX) or Formula (XIII) with the corresponding primary amine of Formula (X) or Formula (XII) under dehydration conditions or dehydration conditions employing normally acidic reagents, such as hydrogen halides, sulfonic or phosphonic acids, and the like. The aforesaid reactants may be dehydrated by azeotropic removal of water under neutral or acidic conditions in an inert solvent such as toluene, xylenes, and the like. Acidic conditions can be effected by the addition of catalytic to stoichiometric quantities of the aforementioned acidic reagents to the reaction medium. Reaction temperatures for dehydration may range from room temperature to reflux, and reaction times may vary from 1 hour to 10 days.

The corresponding intermediate imine can be subsequently either reduced with reducing agents, such as sodium borohydride and sodium cyanoborohydride to give a compound of Formula (XI) or Formula (XIV), wherein X, $R^1$, $R^5$ and $R^8$ are defined hereinabove and $R^2$ and $R^3$ are hydrogen, or alkylated with nucleophilic alkyl organometallic reagents, such as alkyl Grignard or alkyl lithium reagents, and the like to give compounds of Formula (XI) or Formula (XIV), wherein X, $R^1$, $R^5$ and $R^8$ are defined hereinabove, $R^2$ is lower alkyl and $R^3$ is hydrogen. Inert solvents, such as methanol, ethanol, benzene, tetrahydrofuran, dioxane, diethyl ether, and the like may be employed. Reaction temperatures may range from 0° C. to reflux, and reaction times may vary from instantaneous to 48 hours.

Compounds of Formula (I), wherein Z is oxygen; X is $CR^1$ or N; Y is $C(R^1)(R^2)O$, $OC(R^1)(R^2)$, $C(R^1)(R^2)N(R^3)$ or $N(R^3)C(R^1)(R^2)$; wherein $R^1$, $R^2$ and $R^3$ are independently hydrogen or lower alkyl containing 1 to 10 carbon atoms; $R^4$ is $R^1$, benzyl, benzyl ring substituted with $R^5$, benzyl alpha monosubstituted with $R^1$, benzyl ring substituted with $R^5$ and alpha monosubstituted with $R^1$, phenyl, phenylalkyl containing 2 to 10 carbon atoms in the alkyl group or phenylalkyl ring substituted with $R^5$ and containing 2 to 10 carbon atoms in the alkyl group; wherein $R^5$ is $R^1$, lower alkoxy containing 1 to 10 carbon atoms, halogen, trihalomethyl, $NO_2$, $N(R^1)(R^2)$ or $CON(R^1)(R^2)$ and $R^6$ is $R^1$, can be prepared from intermediates of Formula (XV), wherein $R^6$ is $R^1$, and Formula (VIII) wherein $R^8$ is $OR^1$ or (in the case where $R^8$ is hydroxy) either the free acid or Group Ia or IIa salts, such as the sodium or calcium salt, and the like by art-recognized procedures for amide or peptide bond formation.

The aforementioned amide or peptide bond formation reaction can be effected by activating the carbonyl functionality of Formula (VIII), followed by treatment with a compound of Formula (XV) as defined hereinabove in the presence of or without an inert acid scavenger. Carbonyl activating agents known in the art, such as carbodiimides, a mixture of carbodiimides and 1-hydroxybenzotriazole hydrate, thionyl halides, sulfuryl halides, phosphorous tri-and pentahalides, phosphorousoxytrihalides, oxalyl halides, phosgene or its known equivalents, and the like may be employed. Reaction temperatures may range from −20° C. to reflux and reaction times may vary from 0.25 hours to 72 hours. The reaction may be carried out in a solvent that is inert to all reactants. Solvents include, but are not limited to, N,N-dimethylformamide, dimethylsulfoxide, acetone, toluene, dichloromethane, 1,2-dichloroethane, chloroform, carbon tetrachloride, diethyl ether, diphenyl ether, tetrahydrofuran, dioxane, and the like, or if appropriate no solvent may be employed. Inert acid scavengers such as triethylamine, tributylamine, diisopropylethylamine, sodium bicarbonate, potassium carbonate, basic alumina, zeolites, and the like are typically employed, or, if appropriate, no acid scavengers may be employed.

Compounds of Formula (I), wherein X is $CR^1$ or N; Y is $C(R^1)(R^2)O$, $OC(R^1)(R^2)$, $C(R^1)(R^2)N(R^3)$ or $N(R^3)C(R^1)(R^2)$; wherein $R^1$, $R^2$ and $R^3$ are independently hydrogen or lower alkyl containing 1 to 10 carbon atoms; $R^4$ is $R^1$, benzyl, benzyl ring substituted with $R^5$, benzyl alpha monosubstituted with $R^1$, benzyl ring substituted with $R^5$ and alpha monosubstituted with $R^1$, phenyl, phenylalkyl containing 2 to 10 carbon atoms in the alkyl group or phenylalkyl ring substituted with $R^5$ and containing 2 to 10 carbon atoms in the alkyl group; wherein $R^5$ is $R^1$, lower alkoxy containing 1 to 10 carbon atoms, halogen, trihalomethyl, $NO_2$, $N(R^1)(R^2)$ or $CON(R^1)(R^2)$; $R^6$ is hydrogen and Z is $(R^1)(R^2)$, can be prepared by condensation of an aldehyde or ketone of Formula (VIII) wherein $R^8$ is $R^1$ with a primary amine of Formula (XV), wherein $R^6$ is hydrogen, to form the corresponding imine. The imine is subsequently either reduced to give a compound of Formula (I), wherein Z is $(R^1)(R^2)$ and wherein further $R^2$ is hydrogen, and $R^6$ is hydrogen, or alkylated with nucleophilic alkyl organometallic reagents, such as alkyl Grignard or alkyl lithium reagents, and the like to give a compound of Formula (I), wherein Z is $(R^1)(R^2)$ and wherein further $R^2$ is lower alkyl, and $R^6$ is hydrogen.

The aforementioned condensation reaction to form the imines with subsequent reduction to the amines can be conveniently carried out in a single reaction step by mixing the aldehyde or ketone of Formula (VIII), wherein $R^8$ is $R^1$, with the primary amine of Formula (XV), wherein $R^6$ is hydrogen, under hydrogenation conditions. The aforesaid reactants can be hydrogenated over noble metal catalysts, such as platinum, palladium, rhodium, ruthenium, and the like, and the two stages occur under such conditions to produce the desired end products of Formula (I). Common hydrogenation solvents, such as methanol, ethanol, toluene, dichloromethane, chloroform, tetrahydrofuran, dioxane, diethyl ether, and the like may be employed at temperatures from room temperature to the reflux temperature of the reaction mixture.

Alternatively, the aforementioned condensation reaction to form the imines with subsequent reduction or alkylation to the amines can be conveniently carried out in two reaction steps by mixing the aldehyde or ketone of Formula (VIII), wherein $R^8$ is $R^1$, with the primary amine of Formula (XV), wherein $R^6$ is hydrogen, under dehydration conditions or dehydration conditions employing normally acidic reagents, such as hydrogen halides, sulfonic or phosphoric acids, and the like. The aforesaid reactants can be dehydrated by azeotropic removal of water under neutral or acidic conditions in an inert solvent, such as toluene, xylenes, and the like. Acidic conditions may be effected by the addition of catalytic to stoichiometric quantities of the aforementioned acidic reagents to the reaction medium. Reaction temperatures for dehydration may range from room temperature to reflux, and reaction times may vary from 1 hour to 10 days.

The intermediate imine can be subsequently either reduced with reducing agents, such as sodium borohydride, sodium cyanoborohydride, and the like, or alkylated with nucleophilic alkyl organometallic reagents, such as alkyl Grignard or alkyl lithium reagents, and the like to give compounds of Formula (I) as defined hereinabove. Inert solvents, such as methanol, ethanol, tetrahydrofuran, dioxane, diethyl ether, and the like may be employed. Reaction temperatures range from 0° C. to reflux, and reaction times vary from instantaneous to 48 hours.

The products of Formula (I), wherein $R^6$ is hydrogen, can be alkylated with alkylating agents known in the art, such as alkyl iodides, to form compounds of Formula (I), wherein $R^6$ is lower alkyl. The products of Formula (I), wherein $R^6$ is hydrogen and Z is $(R^1)(R^2)$, can be acylated with acylating agents known in the art, such as trifluoroacetyl halide, butyryl halide, trifluoroacetic anhydride, butyric anhydride, and the like in the presence of or without inert acid scavengers, such as triethylamine, tributylamine, diisopropylethylamine, sodium bicarbonate, potassium carbonate, basic alumina, zeolites, and the like to form compounds of Formula (I), wherein $R^6$ is trifluoroacetyl, lower alkyl carbonyl, lower perfluoroalkyl carbonyl, phenyl carbonyl or phenyl lower alkyl carbonyl, and Z is $(R^1)(R^2)$.

Intermediates of Formula (VIII), wherein Y is $CR^1=CR^2$, can be prepared by procedures recognized in the art from known compounds or readily prepared intermediates. An exemplary general procedure (Scheme III) is as follows:

Scheme III

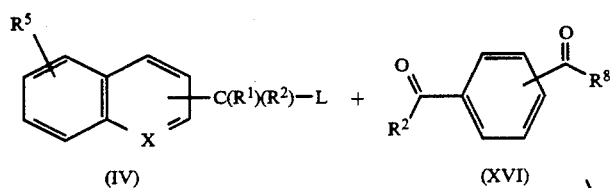

(IV)    (XVI)

-continued
Scheme III

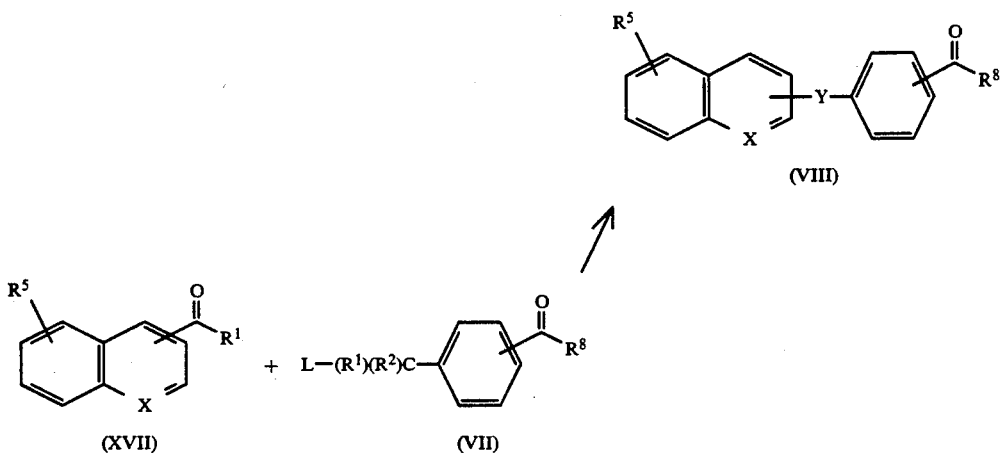

wherein, X, $R^1$, $R^2$, $R^5$, and $R^8$ are defined hereinabove, and wherein Y is $CR^1=CR^2$; $R^2$ is hydrogen in compounds of Formula (IV); $R^1$ is hydrogen in compounds of Formula (VII), and L is a leaving group, such as halo, tosylate, or mesylate. Reaction comditions are those known in the art as Wittig reaction conditions and modifications thereof, such as Horner-Emmons modifications, and the like.

The aforesaid reactants of Formulas (IV) (Scheme III), wherein $R^2$ is hydrogen, can form reactive intermediate phosphorous ylides upon treatment with triphenylphosphine or its known reaction equivalents, such as trialkylphosphonates, followed by treatment with a base, such as triethylamine, diisopropylethyl amine, sodium bicarbonate, potassium carbonate, lithium diisopropylamide, $KN(SiMe_3)_2$, or n-alkyl or aryl lithiums. The intermediate ylides in the presence of compounds of Formula (XVI) form intermediates of Formula (VIII), wherein Y is $CR^1=CR^2$.

Alternatively, the aforesaid reactants of Formula (VII) (Scheme III), wherein $R^1$ is hydrogen, can form reactive intermediate phosphorous ylides upon treatment with triphenylphosphine or its known reaction equivalents, such as trialkylphosphonates, followed by treatment with a base, such as triethylamine, diisopropylethyl amine, sodium bicarbonate, potassium carbonate, lithium diisopropylamide, $KN(SiMe_3)_2$, or n-alkyl or aryl lithiums. The intermediate ylides in the presence of compounds of Formula (XVII) form intermediate compounds of Formula (VIII), wherein Y is $CR^1=CR^2$. If any aldehyde or ketone carbonyl groups present in Formulas (XVI) or (VII) are incompatible with the Wittig reaction conditions and modifications described herein, they may be protected with suitable protecting groups, such as acetal or ketal protecting groups, examples of which may be found in "Protective Groups in Organic Synthesis" by T. W. Green, John Wiley and Sons, 1981. Reaction temperatures may range from −78° C. to reflux and reaction times may vary from 0.25 hour to 72 hours. The reaction may be carried out in a solvent that is inert to all reactants. Solvents include, but are not limited to N,N-dimethylformamide, dimethylsulfoxide, toluene, diethyl ether, diphenyl ether, tetrahydrofuran, dioxane, dichloromethane, 1,2-dichloroethane, chloroform, carbon tetrachloride, and the like, or, if appropriate, no solvent may be employed.

Compounds of Formula (I), wherein Y is $CR^1=CR^2$, can be prepared as described above from intermediates of Formula (VIII), wherein Y is $CR^1=CR^2$.

Compounds of Formula (I), wherein X is NO, may be prepared from appropriate intermediates of Formulas (IV), (VI), (VIII), or (I), wherein X is nitrogen, by oxidation reactions employing oxidizing agents, such as peroxides, alkyl or arylperoxyacids, and the like. The aforesaid reactants can be oxidized to the N-oxides employing hydrogen peroxide, 3-chloroperoxybenzoic acid, peroxyacetic acid, and the like in an inert solvent. Reaction temperatures may range from −20° C. to reflux and reaction times may vary from 0.25 hour to 72 hours. Solvents include, but are not limited to, diethyl ether, diphenyl ether, tetrahydrofuran, dioxane, dichloromethane, 1,2-dichloroethane, chloroform, acetone, toluene, methanol, ethanol, acetic acid, water, and the like, or if appropriate, no solvent may be employed.

The present compounds form salts with acids when a basic amine function is present and salts with bases when an acid function, i.e. carboxyl, is present. All such salts are useful in the isolation and/or purification of the new products. Of particular value are the pharmaceutically acceptable salts with acids as further defined hereinbelow.

Various substituents on the present new compounds, e.g. as defined in $R^1$, $R^2$, $R^3$, $R^4$, $R^5$, and $R^6$ can be present in starting compounds, added to any one of the intermediates, or added after formation of the final products by known methods of substitution or conversion reactions. If the substituents themselves are reactive, then the substituents, or any functional groups which may be incompatible with the reaction conditions, may themselves be protected according to the techniques known in the art. A variety of protecting groups known in the art may be employed. Examples of many of these possible groups may be found in "Protective Groups in Organic Synthesis" by T. W. Green, John Wiley and Sons, 1981. For example, the nitro group can be added to the aromatic ring by nitration and the nitro group converted to other groups, such as amino by reduction, and halo by diazotization of the amino group and replacement of the diazo group. Alkanoyl groups can be substituted onto the aryl groups by Friedel-Crafts acrylation. The acyl groups can then be transformed to the corresponding alkyl groups by various methods, including the Wolff-Kishner reduction and Clemmenson reduction. Amino groups can be alkylated to form mono and dialkylamino groups, and hydroxy groups can be alkylated to form corresponding ethers. Primary alcohols can be oxidized by oxidizing agents known in the art to form carboxylic acids or aldehydes, and secondary alcohols can be oxidized to form ketones. Thus substitution or alteration reactions can be employed to provide a variety of substituents throughout the molecule of the starting material, intermediates, or the final product.

The most preferred compounds of structural Formulas (I), (II), and (III) of the present invention are designated:

N-[1-(phenylmethyl)-4-piperidinyl]-4-(4-quinolinylmethoxy)benzamide;
N-[1-(phenylmethyl)-4-piperidinyl]-4-(2-quinolinylmethoxy)benzamide;
N-(1-butyl-4-piperidinyl)-4-(4-quinolinylmethoxy)benzamide;
N-(1-butyl-4-piperidinyl)-4-(2-quinolinylmethoxy)benzamide;
N-[1-(phenylmethyl)-4-piperidinyl]-3-(4-quinolinylmethoxy)benzamide;
N-[1-(phenylmethyl)-4-piperidinyl]-2-(4-quinolinylmethoxy)benzamide;
N-[1-(phenylmethyl)-4-piperidinyl]-3-(2-quinolinylmethoxy)benzamide;
N-[1-(phenylmethyl)-4-piperidinyl]-2-(2-quinolinylmethoxy)benzamide;
N-(1-butyl-4-piperidinyl)-3-(4-quinolinylmethoxy)benzamide;
N-[1-(phenylmethyl)-4-piperidinyl]-4-(1-naphthalenylmethoxy)benzamide;
N-(1-butyl-4-piperidinyl)-4-(1-napthalenylmethoxy)benzamide;
(E)-N-[1-(phenylmethyl)-4-piperidinyl]-4-[2-(4-quinolinyl)ethenyl]benzamide;
(Z)-N-[1-(phenylmethyl)-4-piperidinyl]-4-[2-(4-quinolinyl)ethenyl]benzamide;
N-[1-(phenylmethyl)-4-piperidinyl]-4-(4-quinolinylmethoxy)benzamide N-oxide;
N-[1-[[4-[(diethylamino)carbonyl]phenyl]methyl]-4-piperidinyl]-4-(4-quinolinylmethoxy)benzamide;
1-(phenylmethyl)-N-[[4-(4-quinolinylmethoxy)phenyl]methyl]-4-piperidinamine;
N-[1-(phenylmethyl)-4-piperidinyl]-N-[[4-(4-quinolinylmethoxy)phenyl]methyl]butanamide;
N-[1-(phenylmethyl)-4-piperidinyl]-4-[(4-quinolinylmethyl)amino]benzamide;
N-(1-butyl-4-piperidinyl)-4-[(4-quinolinylmethyl)amino]benzamide; and the pharmaceutically acceptable acid addition salts thereof.

The present compounds form salts with acids. Suitable acids include, for example, hydrochloric, sulfuric, nitric, benzenesulfonic, toluenesulfonic, acetic, malic, tartaric and the like which are pharmaceutically acceptable.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between 50 and 300 mg of active compound.

The tablets, troches, pills, capsules, and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained release preparations and formulations.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 $\mu$M/kg/day, or from about 0.1 mg to about 50 mg/kg of body weight per day and higher, although it may be administered in several different dosage units. Higher dosages are required for oral administration.

The following Examples further illustrate this invention.

EXAMPLE 1

N-[1-(Phenylmethyl)-4-piperidinyl]-4-(4-quinolinylmethoxy)benzamide

Step a) Preparation of 4-Quinolinemethanol

A solution of 4-quinolinecarboxaldehyde (55.0 g, 35 mmol) in ether (1 L) was added dropwise over 0.25 hours to a mechanically stirred biphasic solution of $NaBH_4$ (13.24 g, 35 mmol), water (500 mL), and ether (100 mL) at 0° C. After 15 minutes, a second equivalent of $NaBH_4$ (13.24 g, 35 mmol) dissolved in water was added, and the reaction allowed to warm to room temperature over 0.25 hour. The aqueous layer was separated, extracted with $CH_2Cl_2$ (2×1 L), and the combined organic layer washed with water (500 mL), dried ($MgSO_4$), filtered, and evaporated to a solid residue. Crystallization from methylene chloride-ether-hexane afforded 21.7 g (13.6 mmol, 39%) of a white solid. The filtrate was concentrated, and following HPLC separation, crystallization afforded 14.1 g (8.9 mmol, 25%) of a second crop, (35.8 g, 64% total yield), m.p. 95°-97° C.

$^1$H NMR ($CDCl_3$, 400 MHz) δ: 8.79 (d, J=4.4 Hz, 1H), 8.10 (d, J=8.4 Hz, 1H), 7.94 (dd, J=8.4, 0.8 Hz, 1H), 7.70 (td, J=8.3, 1.4 Hz, 1H), 7.55 (td, J=8.5, 1.2 Hz, 1H), 7.54 (d, J=4.7 Hz, 1H), 5.23 (s, 2H), 3.80 (bs, 1H)

MS (EI), m/z (rel. intensity)=159 ($M^+$, 58), 130 (100)

IR (KBr) ν: 3280, 2830, 1585 $cm^{-1}$

Anal. Calcd. for $C_{10}H_9NO$: C, 75.45; H, 5.70; N, 8.80. Found: C, 75.70; H, 5.65; N, 8.84.

Step b) Preparation of 4-(Chloromethyl)quinoline Hydrochloride

4-Quinolinemethanol (21.5 g, 135 mmol) was treated with thionyl chloride (32.12 g, 270 mmol) in 500 mL of methylene chloride and refluxed for 0.5 hour. The reaction was cooled to 0° C. for 1 hour, filtered and washed with cold methylene chloride and ether to afford, after air-drying, 13.87 g (65 mmol, 48% yield) of the product as a dark tan solid, m.p. 193°-195° C. (dec).

$^1$H NMR (DMSO-$d_6$, 400 MHz) δ: 12.3 (br s, 1H), 9.26 (d, J=5.3 Hz, 1H), 8.47 (d, J=9.5 Hz, 1H), 8.46 (d, J=9.8 Hz, 1H), 8.13 (d, J=5.3 Hz, 1H), 8.11 (ddd, J=8.3, 7.0, 1.3 Hz, 1H), 7.97 (ddd, J=8.0, 7.0, 1.0 Hz, 1H), 5.52 (s, 2H)

MS(EI), m/z (rel. intensity)=179 (25), 177 ($M^+$, 67), 159 (37), 142 (100), 130 (77) IR (KBr) ν: 3440, 2940, 2900, 2470, 1605, 1545, 1385, 1280, 1220, 840, 750 $cm^{-1}$ Anal. Calcd. for $C_{10}H_8ClN \cdot HCl$: C, 56.10; H, 4.24; N, 6.54. Found: C, 56.01; H, 4.10; N, 6.39.

Step c) Preparation of 4-(4-Quinolinylmethoxy)benzoic Acid Methyl Ester

Methyl-4-hydroxybenzoate (7.60 g, 50 mmol) was added to a stirred, hexane-washed suspension of 80% NaH (1.5 g, 50 mmol) in 50 mL of dry DMF at 0° C., followed, after 15 minutes, by the dropwise addition of 4-(chloromethyl)quinoline (8.0 g, 45 mmol), [converted to the free base from the hydrochloride salt (10.71 g, 50 mmol) by extraction with cold 1N NaOH (75 mL) in ether (200 mL), followed by drying ($MgSO_4$) and evaporation to an oil]. The reaction was heated at 130° C. for 0.5 hour. After cooling, the mixture was poured into 1N NaOH and extracted with methylene chloride (3×200 mL); the combined organic layer was washed with water (2×50 mL), dried (MgSO4), filtered, and evaporated to a residue, which, after recrystallization (dichloromethane-ether, 2X) and drying in vacuo (6 hours at 80° C.) overnight, afforded 5.2 g (17.8 mmol, 40% yield) of a white fluffy solid, m.p. 133°-135° C.

$^1$H NMR ($CDCl_3$, 400 MHz) δ: 8.93 (d, J=4.4 Hz, 1H), 8.18 (d, J=8.8 Hz, 1H), 8.03 (d, J=8.8 Hz, 2H), 7.97 (dd, J=8.4, 0.7 Hz, 1H), 7.77 (ddd, J=8.2, 7.0, 1.2 Hz, 1H), 7.62 (ddd, J=8.2, 7.0 1.2 Hz, 1H), 7.54 (d, J=4.4 Hz, 1H), 7.05 (d, J=8.8 Hz, 2H), 5.60 (s, 2H), 3.89 (s, 3H)

MS(EI), m/z (rel intensity)=293 ($M^+$, 8), 142 (100), 115 (42)

IR (KBr) ν: 3005, 2950, 1715, 1605, 1510, 1435, 1285, 1240, 1170 $cm^{-1}$

Anal. Calcd. for $C_{18}H_{15}NO_3$: C, 73.71; H, 5.15; N, 4.77. Found: C, 73.99; H, 5.02; N, 4.81.

Step d) Preparation of 4-(4-Quinolinylmethoxy)benzoic Acid Sodium Salt Hydrate 4-(4-Quinolinylmethoxy)benzoic acid, methyl ester (5.28 g, 18 mmol) in 200 mL of MeOH was treated slowly at reflux with 2.5N NaOH (aq) (36 mL, 90 mmol). The mixture was refluxed for 2 hours, filtered, and evaporated to a residue. Crystallization from water (twice) afforded the product as a white crystalline solid, 4.98 g (16.3 mmol, 91% yield), m.p.>250° C.

$^1$H NMR (DMSO-$d_6$, 400 MHz) δ: 8.89 (d, J=4.3 Hz, 1H), 8.17 (d, J=8.3 Hz, 1H), 8.06 (d, J=8.3 Hz, 1H), 7.87 (d, J=8.7 Hz, 2H), 7.79 (ddd, J=8.2, 6.9, 1.3 Hz, 1H), 7.66 (ddd, J=8.2, 6.9, 1.3 Hz, 1H), 7.64 (d, J=4.3 Hz, 1H), 7.01 (d, J=8.7 Hz, 2H), 5.66 (s, 2H), 3.40 (bs, 1H)

MS (−FAB), m/z (rel. intensity)=278 ($M^−$, 40)

Karl Fisher 1.40% $H_2O$

IR (KBr) ν: 3420, 1605, 1555, 1400, 1250, 850 $cm^{-1}$

Anal. Calcd. for $C_{17}H_{12}NNaO_3 \cdot 0.25 H_2O$: C, 66.78; H, 4.12; N, 4.58. Found: C, 66.59; H, 3.91; N, 4.59.

Step e) Preparation of N-[1-(Phenylmethyl)-4-piperidinyl]-4(4-quinolinylmethoxy)benzamide 4-(4-Quinolinylmethoxy)benzoic acid sodium salt (7.53 g, 25 mmol) was treated with thionyl chloride (8.92 g, 75 mmol) in 200 mL of dichloroethane and refluxed for 25 minutes under nitrogen. After cooling to 0° C., 4-(4-quinolinylmethoxy)benzoyl chloride hydrochloride was filtered and washed with cold dichloroethane and ether. The acid chloride, resuspended in methylene chloride, was treated with 4-amino-1-benzylpiperidine (9.51 g, 50 mmol) and filtered after 1 hour. The filtrate was extracted sequentially with 1N NaOH (aq) (2×75 mL) and water (3×150 mL), dried ($MgSO_4$), and evaporated to a residue. Recrystallization from methylene chloride-ether-hexane (3×) and MeOH (3×) afforded 6.2 g (13.7 mmol, 55% yield) of the product as a white solid, m.p. 161°-163° C.

$^1$H NMR ($CDCl_3$, 400 MHz) δ: 8.92 (d, J=4.4 Hz, 1H), 8.18 (d, J=8.4 Hz, 1H), 7.97 (dd, J=8.4, 0.6 Hz, 1H), 7.77 (td, J=8.1, 0.8 Hz, 1H), 7.74 (d, J=8.6 Hz, 2H), 7.62 (td, J=8.1, 0.8 Hz, 1H), 7.54 (d, J=4.4 Hz, 1H), 7.31 (m, 4H), 7.26 (m, 1H), 7.05 (d, J=8.8 Hz, 2H), 5.89 (d, J=7.9 Hz, 1H), 5.60 (s, 2H), 4.00 (m, 1H), 3.51 (s, 2H), 2.85 (d, J=11.7 Hz, 2H), 2.17 (t, J=10.6 Hz, 2H), 2.01 (d, J=12.7 Hz, 2H), 1.55 (qd J=11.7, 3.8 Hz, 2H)

MS (CI), m/z (rel. intensity)=452 ($MH^+$, 4), 311 (100)

IR (KBr) ν: 3440, 3270, 2910, 2790, 1628, 1605, 1540, 1500, 1235 $cm^{-1}$

Anal. Calcd. for $C_{29}H_{29}N_3O_2$: C, 77.13; H, 6.47; N, 9.30. Found: C, 77.46; H, 6.61; N, 9.37.

EXAMPLE 2

N-[1-(Phenylmethyl)-4-piperidinyl]-4-(2-quinolinylmethoxy)benzamide

Step a) Preparation of 4-(2-Quinolinylmethoxy)benzoic Acid Methyl Ester

The title compound was prepared as described in Example 1c by substituting 2-(chloromethyl)quinoline for 4-(chloromethyl)quinoline. Repeated recrystallization from methylene chloride-ether-hexane afforded the product as a white fluffy solid in 59% yield, m.p. 112°–113° C.

$^1$H NMR (CDCl$_3$, 400 MHz) δ: 8.19 (d, J=8.5, 1H), 8.08 (dd, J=8.4, 0.5 Hz, 1H), 7.99 (d, J=8.9 Hz, 2H), 7.83 (dd, J=8.2, 1.1 Hz, 1H), 7.75 (ddd, J=8.4, 7.0, 1.4 Hz, 1H), 7.63 (d, J=8.5 Hz, 1H), 7.56 (ddd, J=8.0, 6.9, 1.1 Hz, 1H), 7.05 (d, J=9.0 Hz, 2H); 5.43 (s, 2H), 3.87 (s, 3H)

MS (EI), m/z (rel. intensity)=293 (M+, 60), 142 (100)

IR (KBr) v: 2950, 2910, 1715, 1605, 1510, 1290, 1250 cm$^{-1}$

Anal. Calcd. for C$_{18}$H$_{15}$NO$_3$: C, 73.71; H, 5.15; N, 4.77. Found: C, 73.82; H, 5.27; N, 4.84.

Step b) Preparation of 4-(2-Quinolinylmethoxy)benzoic Acid 4-(2-Quinolinylmethoxy)benzoic acid methyl ester (19.7 g, 67.2 mmol) in 500 mL of MeOH was treated slowly at reflux with 2.5N NaOH (aq) (135 mL, 337 mmol). The reaction was refluxed for 2 hours, filtered, and evaporated to a residue. Crystallization from water afforded 15.7 g (52 mmol, 78% yield) of the sodium salt as a white solid. Treatment of the sodium salt with 1 equivalent of 1N HCl (aq) in MeOH afforded, after recrystallization from ethyl acetate-ether-hexane and drying in vacuo (6 hours at 90° C.) overnight, the free acid as a white solid, m.p. 206°–208° C. $^1$H NMR (DMSO-d$_6$, 400 MHz) δ: 12.64 (bs, 1H), 8.41 (d, J=8.5 Hz, 1H), 8.01 (d, J=8.9 Hz, 1H), 7.99 (d, J=9.4 Hz, 1H), 7.89 (d, J=8.8 Hz, 2H), 7.78 (ddd, J=8.3, 6.9, 1.4 Hz, 1H), 7.66 (d, J=8.5 Hz, 1H), 7.62 (ddd, J=8.1, 7.0, 1.1 Hz, 1H), 7.15 (d, J=8.9 Hz, 2H), 5.44 (s, 2H)

MS (EI), m/z (rel. intensity)=279 (M+, 42), 142 (100)

IR (KBr) v: 2670, 2550, 1685, 1605, 1505, 1428, 1250, 1175, 1065 cm$^{-1}$

Anal. Calcd. for C$_{17}$H$_{13}$NO$_3$: C, 73.11; H, 4.69; N, 5.02. Found: C, 73.30; H, 4.60; N, 5.03.

Step c) Preparation of 4-[1-(Phenylmethyl)-4-piperidinyl]-4-(2-quinolinylmethoxy)benzamide 4-(2-Quinolinylmethoxy)benzoic acid sodium salt (3.01 g, 10 mmol) was refluxed in excess thionyl chloride (neat) for 10 minutes. The thionyl chloride was removed and the residue, resuspended in methylene chloride, was treated with 4-amino-1-benzylpiperidine (4.75 g, 25 mmol). After 15 minutes, the reaction was extracted with 1N NaOH (aq) (2×75 mL), and water (3×100 mL), dried (MgSO$_4$), and evaporated to a semi-solid which upon trituration with ether afforded 3.7 g (8.2 mmol, 82% yield) of a white amorphous solid. Recrystallization from methylene chloride-ether and MeOH afforded the product as a white crystalline solid, m.p. (158-160) 165°–167° C.

$^1$H NMR (CDCl$_3$, 400 MHz) δ: 8.18 (d, J=8.5 Hz, 1H), 8.08 (d, J=8.4 Hz, 1H), 7.83 (d, J=8.1 Hz, 1H), 7.74 (ddd, J=8.3, 6.9, 1.4 Hz, 1H), 7.70 (d, J=8.8 Hz, 2H), 7.63 (d, J=8.5 Hz, 1H), 7.56 (dt, J=8.0, 1.0 Hz, 1H), 7.31 (m, 4H), 7.26 (m, 1H), 7.04 (d, J=8.8 Hz, 2H), 5.86 (bd, J=7.9 Hz, 1H), 5.42 (s, 2H), 3.98 (m, 1H), 3.51 (s, 2H), 2.83 (bd, J=11.8 Hz, 2H), 2.17 (t, J=11.3 Hz, 2H), 1.99 (bd, J=12.6 Hz, 2H), 1.53 (qd, J=11.4, 3.7 Hz, 2H)

MS (EI), m/z (rel. intensity)=451 (M+, 30), 279 (56), 91 (100)

IR (KBr) v: 3330, 2940, 2770, 1630, 1610, 1505, 1265 cm$^{-1}$

Anal. Calcd. for: C$_{29}$H$_{29}$N$_3$O$_2$: C, 77.13; H, 6.47; N, 9.30. Found: C, 76,91; H, 6.41; N, 9.14.

EXAMPLE 3

N-(1-Butyl-4-piperidinyl)-4-(4-quinolinylmethoxy)benzamide

The title compound was prepared as described in Example 1e by substituting 4-amino-1-butylpiperidine for 4-amino-1-benzylpiperidine. Recrystallation from methylene chloride-ether and acetonitrile afforded the product as a white solid in 62% yield, m.p. 176°–177° C.

$^1$H NMR (CDCl$_3$, 400 MHz) δ: 8.93 (d, J=4.4 Hz, 1H), 8.18 (d, J=8.4 Hz, 1H); 7.98 (d, J=8.4 Hz, 1H), 7.77 (ddd, J=8.2, 6.9, 1.3 Hz, 1H), 7.75 (d, J=8.8 Hz, 2H), 7.62 (ddd, J=8.3, 7.0, 1.3 Hz, 1H), 7.54 (d, J=4.4 Hz, 1H), 7.05 (d, J=8.8 Hz, 2H), 5.89 (d, J=7.9 Hz, 1H), 5.60 (s, 2H), 3.99 (m, 1H), 2.89 (d, J=11.6 Hz, 2H), 2.34 (t, J=7.6 Hz, 2H), 2.12 (t, J=11.4 Hz, 2H), 2.04 (d, J=12.5 Hz, 2H), 1.54 (qd, J=11.4, 3.7 Hz, 2H), 1.48 (p, J=7.8 Hz, 2H), 1.32 (sextet, J=7.6 Hz, 2H), 0.92 (t, J=7.3 Hz, 3H)

MS (+FAB), m/z (rel. intensity)=418 (M+, 50), 138 (100)

IR (KBr) v: 3320, 2940, 1635, 1520, 1250, 850 cm$^{-1}$

Anal. Calcd. for C$_{26}$H$_{31}$N$_3$O$_2$: C, 74.79; H, 7.48; N, 10.06. Found: C, 74.63; H, 7.50; N, 10.05.

EXAMPLE 4

N-(1-Butyl-4-piperidinyl)-4-(2-quinolinylmethoxy)benzamide 4-(2-Quinolinylmethoxy)benzoic acid sodium salt (3.01 g, 10 mmol) was treated with thionyl chloride (2.4 g, 20 mmol) in 200 mL of dichloroethane and refluxed for 15 minutes under nitrogen. After cooling to −10° C., 4-(2-quinolinylmethoxy)benzoyl chloride hydrochloride was filtered and washed with cold dichloroethane and ether. The acid chloride, resuspended in methylene chloride, was treated with 4-amino-1-butylpiperidine (1.56 g, 10 mmol) and, after 2 hours, extracted with 1N NaOH (aq) and water. Evaporation of the organic phase and recrystallization of the residue from methylene chloride-ether and acetonitrile afforded, after drying in vacuo overnight (6 hours at 80° C.), 2.7 g (6.5 mmol, 65% yield) of the product as a white solid, m.p. 171.5°–173° C.

$^1$H NMR (CDCl$_3$, 400 MHz) δ: 8.17 (d, J=8.5 Hz, 1H), 8.07 (dd, J=8.5, 0.8 Hz, 1H), 7.82 (dd, J=8.3, 1.3 Hz, 1H), 7.74 (ddd, J=8.7, 7.0, 1.7 Hz, 1H), 7.70 (d, J=8.9 Hz, 2H), 7.62 (d, J=8.5 Hz, 1H), 7.55 (ddd, J=8.2, 7.0, 1.2 Hz, 1H), 7.03 (d, J=8.9 Hz, 2H), 5.89 (d, J=8.1 Hz, 1H), 5.41 (s, 2H), 3.96 (m, 1H), 2.86 (d, J=12.0 Hz, 2H), 2.31 (t, J=7.7 Hz, 2H), 2.09 (td, J=11.4, 1.5 Hz, 2H), 2.01 (d, J=12.9 Hz, 2H), 1.51 (qd, J=12.9, 3.5 Hz, 2H), 1.46 (p, J=7.5 Hz, 2H), 1.30 (sextet, J=7.3 Hz, 2H), 0.91 (t, J=7.3 Hz, 3H MS (EI), m/z (rel. intensity)=417 (M+, 25), 374 (100), 262 (65)

IR (KBr) v: 3280, 2920, 1625, 1605, 1535, 1505, 1240 825 cm$^{-1}$

Anal. Calcd. for $C_{26}H_{31}N_3O_2$: C, 74.79; H, 7.48; N, 10.06. Found: C, 74.93, H, 7.62, N, 10.33.

EXAMPLE 5

N-[1-(Phenylmethyl)-4-piperidinyl]-3-(4-quinolinylmethoxy)benzamide

Step a) Preparation of 3-(4-Quinolinylmethoxy)benzoic Acid Methyl Ester

A stirred suspension of lepidine (4-methylquinoline, 57.28 g, 400 mmol) and N-bromosuccinimide (71.20 g, 400 mmol) in 1.5 L of carbon tetrachloride was treated with benzoyl peroxide (3 g, 12.4 mmol) in two aliquots and the mixture irradiated with a 300 watt floodlight at 90° C. for 6 hours. The reaction was cooled, filtered, and evaporated to an oily residue. The residue was treated with methyl 3-hydroxybenzoate (30.43 g, 200 mmol), cesium carbonate (65.16 g, 200 mmol), and potassium iodide (3.32 g, 20 mmol) in acetone and refluxed for 4 hours. The solvent was removed in vacuo and the residue extracted with methylene chloride and water (3×). The organic phase was dried (MgSO$_4$), evaporated, and, after trituration with hexane, purified by flash column chromatography to afford 10.25 g (35 mmol, 17% yield) of the product as an off-white solid. Recrystallization from acetonitrile afforded an analytically pure sample, m.p. 103°–105° C.

$^1$H NMR (CDCl$_3$, 400 MHz) δ: 8.92 (d, J=4.4 Hz, 1H), 8.16 (d, J=8.3 Hz, 1H), 7.98 (dd, J=8.5, 1.2 Hz, 1H), 7.75 (ddd, J=8.0, 6.8, 1.2 Hz, 1H), 7.72 (m, 1H), 7.70 (dt, J=7.7, 1.2 Hz, 1H), 7.60 (ddd, J=8.0, 6.8, 1.2 Hz, 1H), 7.56 (d, J=4.4 Hz, 1H), 7.36 (t, J=8.1 Hz, 1H), 7.21 (ddd, J=8.3, 2.7, 1.0 Hz, 1H), 5.57 (s, 2H), 3.91 (s, 3H)

MS (EI), m/z (rel. intensity)=293 (M$^+$, 9), 142 (100), 115 (28) IR (KBr) v: 3420, 2940, 1705, 1580, 1440, 1295, 1280, 1100, 1060, 740 cm$^{-1}$ Anal. Calcd. for $C_{18}H_{15}NO_3$: C, 73.71; H, 5.15; N, 4.78. Found: C, 74.00; H, 5.06, N, 4.63.

Step b) Preparation of N-[1-(Phenylmethyl)-4-piperidinyl]-3-(4-quinolinylmethoxy)benzamide 3-(4-Quinolinylmethoxy)benzoic acid methyl ester (10.25 g, 35 mmol) and 2.5N NaOH (aq) (70 ml, 175 mmol) were refluxed for 2 hours in MeOH (300 mL). Neutralization with conc. HCl (14.5 mL, 175 mmol) and filtration afforded 9.5 g (34 mmol, 97%) of air-dried 3-(4-quinolinylmethoxy)benzoic acid as a white solid. The free acid (9.0 g, 32 mmol) was refluxed in excess thionyl chloride (50 mL, neat) for 10 minutes. Dichloroethane and ether were added and the resulting precipitate filtered to afford 3-(4-quinolinylmethoxy)benzoyl chloride hydrochloride as a cream colored solid. The acid chloride (3.34 g, 10 mmol), resuspended in methylene chloride, was treated with 4-amino-1-benzylpiperidine (3.80 g, 20 mmol) and, after 0.5 hours, extracted with 1N NaOH (aq) and water. Evaporation of the organic phase, crystallization of the residue from methylene chloride-ether-hexane, and purification by flash column chromatography on silica gel afforded, after recrystallization from acetonitrile, 3.1 g (6.9 mmol, 69% yield) of the product as a pale yellow solid, m.p. 160°–163° C.

$^1$H NMR (CDCl$_3$, 400 MHz) δ: 8.91 (d, J=4.4 Hz, 1H), 8.15 (dd, J=8.5, 0.6 Hz, 1H), 7.96 (ddd, J=8.3, 1.2, 0.6 Hz, 1H), 7.74 (ddd, J=8.5, 7.1, 1.4 Hz, 1H), 7.59 (ddd, J=8.3, 7.1, 1.2 Hz, 1H), 7.55 (d, J=4.4 Hz, 1H), 7.51 (dd, J=2.5, 1.7 Hz, 1H), 7.35 (t, J=7.8 Hz, 1H), 7.31 (d, J=7.5 Hz, 1H), 7.30 (m, 4H), 7.25 (m, 1H), 7.13 (ddd, J=7.9, 2.5, 1.0 Hz, 1H), 6.03 (d, J=7.9 Hz, 1H), 5.56 (s, 2H), 3.99 (m, 1H), 3.50 (s, 2H), 2.83 (d, J=11.8 Hz, 2H), 2.16 (td, J=11.4, 1.9 Hz, 2H), 2.01 (d, J=11.6 Hz, 2H), 1.54 (qd, J=11.4, 3.7 Hz, 2H)

MS(CI), m/z (rel. intensity)=452 (MH$^+$, 10), 353 (5), 311 (100), 144 (75)

IR (KBr): v: 3450, 3330, 2980, 1640, 1595, 1545, 1335, 1260, 1150, 1070, 760 cm$^{-1}$

Anal. Calcd. for $C_{29}H_{29}N_3O_2$: C, 77.14; H, 6.47; N, 9.31. Found: C, 76.87; H, 6.51; N, 9.60.

EXAMPLE 6

N-[1-(Phenylmethyl)-4-piperidinyl]-2-(4-quinolinylmethoxy)benzamide

Step a) Preparation of 2-(4-Quinolinylmethoxy)benzoic Acid Methyl Ester

A mixture of methyl salicylate (3.04 g, 20 mmol), cesium carbonate (6.50 g, 20 mmol), potassium iodide (0.67 g, 4.0 mmol) and 4-(chloromethyl)quinoline (3.55 g, 20 mmol) [converted to the free base from the hydrochloride salt (4.70 g, 22 mmol) by extraction with 1N NaOH in ether, followed by drying (MgSO$_4$) and evaporation to an oil] was suspended in acetone (700 mL) and refluxed for 6 hours. After removal of the solvent in vacuo, the residue was suspended in methylene chloride or ether and extracted with 1N NaOH (2×200 mL) and water (2×200 mL). The combined organic phase was dried (MgSO$_4$) evaporated to a yellow oil, and crystallized from methylene chloride-ether-hexane to afford 5.15 g (17.6 mmol, 88% yield) of the product as a white solid, m.p. 93°–95° C.

$^1$H NMR (CDCl$_3$, 400 MHz) δ: 8.94 (d, J=4.6 Hz, 1H), 8.15 (dd, J=8.5, 0.4 Hz, 1H), 7.95 (ddd, J=8.3, 1.2, 0.6 Hz, 1H), 7.87 (dd, J=7.7, 1.7 Hz, 1H), 7.81 (d, J=4.4 Hz, 1H), 7.73 (ddd, J=8.5, 7.0, 1.5 Hz, 1H), 7.58 (ddd, J=8.1, 6.9, 1.2 Hz, 1H), 7.46 (ddd, J=9.0, 7.1, 1.9 Hz, 1H), 7.06 (d, J=7.7 Hz, 1H), 7.04 (t, J=7.7 Hz, 1H), 5.63 (s, 2H), 3.88 (s, 3H)

MS (EI), m/z (rel. intensity)=293 (M$^+$, 27), 261 (9), 142 (100), 115 (47)

IR (KBr) v: 3420, 1695, 1600, 1590, 1485, 1450, 1435, 1310, 1250, 1050, 830, 740 cm$^{-1}$

Anal. Calcd. for $C_{18}H_{15}NO_3$: C, 73.71; H, 5.15; N, 4.78. Found: C, 73.78; H, 5.28; N, 4.62.

Step b) Preparation of 2-(4-Quinolinylmethoxy)benzoic Acid 2-(4-Quinolinylmethoxy)benzoic acid methyl ester (4.0 g, 13.65 mmol) and 2.5N NaOH (aq) (16 mL, 40 mmol) were refluxed for 2 hours in MeOH (100 mL). Neutralization wih 2N HCl (aq) (20 mL, 40 mmol) and filtration afforded 3.6 g. (12.9 mmol, 94% yield) of the product as a rust colored solid. Recrystallization (DMSO-MeOH) afforded an analytical sample after drying in vacuo, m.p. 210°–211° C. (dec).

$^1$H NMR (DMSO-d$_6$, 400 MHz) δ: 12.77 (br s, 1H), 8.92 (d, J=4.4 Hz, 1H), 8.21 (d, J=8.3 Hz, 1H), 8.06 (d, J=8.4 Hz, 1H), 7.85 (d, J=4.4 Hz, 1H), 7.80 (td, J=8.1, 1.0 Hz, 1H), 7.72 (dd, J=7.6, 1.7 Hz, 1H), 7.66 (td, J=8.1, 1.0 Hz, 1H), 7.54 (td, J=7.9, 1.7 Hz, 1H), 7.42 (d, J=8.4 Hz, 1H), 7.06 (t, J=7.5 Hz, 1H), 5.75 (s, 2H)

MS(EI), m/z (rel. intensity)=279 (M$^+$, 12), 142 (100)

IR (KBr) v: 3420, 2440, 1920, 1670, 1590, 1480, 1440, 1290, 1240, 1050, 840, 750 cm$^{-1}$

Anal. Calcd. for $C_{17}H_{13}NO_3$: C, 73.11; H, 4.69; N, 5.01. Found: C, 72.93; H, 4.67; N, 4.92.

Step c) N-[1-(Phenylmethyl)-4-piperidinyl]-2-(4-quinolinylmethoxy)benzamide

The title compound was prepared as described in Example 4 by substituting 2-(4-quinolinylmethoxy)benzoic acid for 4-(2-quinolinylmethoxy)benzoic acid sodium salt and 4-amino-1-benzylpiperidine for 4-amino-1-butylpiperidine. Recrystallization from acetonitrile and ether-methylene chloride afforded the product, after drying in vacuo, as cream colored needles in 47% yield, m.p. 144°–146° C.

1H NMR (CDCl3, 400 MHz) δ: 8.98 (d, J=4.3 Hz, 1H), 8.22 (dd, J=7.7, 1.8 Hz, 1H), 8.21 (d, J=7.7 Hz, 1H), 7.98 (dd, J=8.4, 0.7 Hz, 1H), 7.79 (ddd, J=8.2, 6.9, 1.3 Hz, 1H), 7.63 (ddd, J=8.2, 7.0, 1.2 Hz, 1H), 7.51 (d, J=4.4 Hz, 1H), 7.47 (td, J=8.3, 2.6 Hz, 2H), 7.29 (m, 2H), 7.23 (m, 3H), 7.15 (t, J=7.7 Hz, 1H), 7.11 (d, J=8.4 Hz, 1H), 5.60 (s, 2H), 3.81 (m, 1H), 3.26 (s, 2H), 2.30 (br s, 2H), 1.95 (td, J=1.25, 2.7 Hz, 2H), 1.57 (dd, J=12.8, 3.8 Hz, 2H), 0.88 (q, J=9.1 Hz, 2H)

MS(CI), m/z (rel. intensity)=452 (MH+, 10), 311 (100), 144 (30)

IR (KBr) ν: 3390, 2940, 1640, 1590, 1515, 1220, 990, 750, 740, 720 cm−1

Anal. Calcd. for C29H29N3O2: C, 77.14; H, 6.47; N, 9.31. Found: C, 77.29; H, 6.39; N, 9.14.

EXAMPLE 7

N-[1-(Phenylmethyl)-4-piperidinyl]-3-(2-quinolinylmethoxy)benzamide

Step a) Preparation of 3-(2-Quinolinylmethoxy)benzoic Acid Methyl Ester

The title compound was prepared as described in Example 6a by substituting 2-(chloromethyl)quinoline for 4-(chloromethyl)quinoline and methyl 3-hydroxybenzoate for methyl salicylate. The product was obtained as a white solid in 68% yield, m.p. 60°–62° C.

1H NMR (CDCl3, 400 MHz) δ: 8.20 (d, J=8.5 Hz, 1H), 8.09 (d, J=8.5 Hz, 1H), 7.83 (dd, J=8.2, 1.0 Hz, 1H), 7.74 (ddd, J=8.3, 6.9, 1.4 Hz, 1H), 7.73 (m, 1H), 7.67 (d, J=8.5 Hz, 1H), 7.66 (ddd, J=7.7, 1.3, 1.0 Hz, 1H), 7.55 (ddd, J=8.0, 6.9, 1.1 Hz, 1H), 7.35 (t, J=8.0 Hz, 1H), 7.22 (ddd, J=8.3, 2.7, 1.0 Hz, 1H), 5.42 (s, 2H), 3.91 (s, 3H)

MS(EI), m/z (rel. intensity)=293 (M+, 13), 158 (4), 142 (100)

IR (KBr) ν: 3400, 3050, 2960, 1725, 1600, 1430, 1240, 1220, 1075, 1050, 820, 750 cm−1

Anal. Calcd. for C18H15NO3: C, 73.71; H, 5.15; N, 4.78. Found: C, 73.74; H, 4.95; N, 4.78.

Step b) 3-(2-Quinolinylmethoxy)benzoic Acid 3-(2-Quinolinylmethoxy)benzoic acid methyl ester (5.86 g, 20 mmol) and 2.5N NaOH (aq) (40 mL, 100 mmol) were refluxed for 3 hours in MeOH (150 mL). Neutralization, while hot, with conc. HCl (8.25 mL, 100 mmol) and filtration of the cooled precipitate afforded 5.02 g (18 mmol, 90% yield) of the product as a white solid, m.p. 187°–190° C.

1H NMR (DMSO-d6, 400 MHz) δ: 13.00 (br s, 1H), 8.41 (d, J=8.5 Hz, 1H), 8.01 (d, J=8.7 Hz, 1H), 7.98 (dd, J=8.2, 0.9 Hz, 1H), 7.78 (ddd, J=8.4, 6.9, 1.5 Hz, 1H), 7.67 (d, J=8.5 Hz, 1H), 7.61 (ddd, J=8.0, 6.9, 1.1 Hz, 1H), 7.57 (dd, J=2.5, 1.4 Hz, 1H), 7.54 (ddd, J=7.6, 1.3, 1.1 Hz, 1H), 7.42 (t, J=8.0 Hz, 1H), 7.30 (ddd, J=8.3, 2.7, 1.0 Hz, 1H), 5.42 (s, 2H)

MS(EI), m/z (rel. intensity)=270 (M+, 23), 158 (2), 142 (100), 115 (25)

IR (KBr) ν: 3440, 3080, 2910, 2550, 1720, 1600, 1510, 1490, 1270, 1220, 1075, 1060, 830, 750 cm−1

Anal. Calcd. for C17H13NO3: C, 73.11; H, 4.69; N, 5.01. Found: C, 73.37; H, 4.69; N, 4.99.

Step c) Preparation of N-[1-(Phenylmethyl)-4-piperidinyl]-3-(2-quinolinylmethoxy)benzamide The title compound was prepared as described in Example 4 by substituting 3-(2-quinolinylmethoxy)benzoic acid for 4-(2-quinolinylmethoxy)benzoic acid sodium salt and 4-amino-1-benzylpiperidine for 4-amino-1-butylpiperidine. The product (3.2 g, 7.1 mmol) was obtained in 40% yield after recrystallization from methylene chloride-ether and acetonitrile and drying in vacuo, m.p. 162°–164° C.

1H NMR (CDCl3, 400 MHz) δ: 8.18 (d, J=8.5 Hz, 1H), 8.08 (d, J=8.4 Hz, 1H), 7.82 (d, J=8.1 Hz, 1H), 7.73 (ddd, J=8.4, 7.0, 1.4 Hz, 1H), 7.64 (d, J=8.5 Hz, 1H), 7.55 (ddd, J=8.0, 7.0, 0.9 Hz, 1H), 7.46 (d, J=1.4 Hz, 1H), 7.31 (m, 6H), 7.26 (m, 1H), 7.13 (dt, J=6.2, 2.8 Hz, 1H), 5.99 (d, J=7.8 Hz, 1H), 5.41 (s, 2H), 3.99 (m, 1H), 3.51 (s, 2H), 2.83 (d, J=11.8 Hz, 2H), 2.16 (t, J=11.2 Hz, 2H), 2.00 (d, J=10.5 Hz, 2H), 1.54 (qd, J=12.0, 3.2 Hz, 2H)

MS(EI), m/z (rel. intensity)=451 (M+, 4), 308 (50), 172 (50), 91 (100)

IR (KBr) ν: 3420, 3230, 3020, 2900, 1620, 1525, 1320, 1235, 1010, 820, 725 cm−1

Anal. Calcd. for C29H29N3O2: C, 77.14; H, 6.47; N, 9.31. Found: C, 76.84; H, 6.39; N, 9.06.

EXAMPLE 8

N-[1-(Phenylmethyl)-4-piperidinyl]-2-(2-quinolinylmethoxy)benzamide

Step a) Preparation of 2-(2-Quinolinylmethoxy)benzoic Acid Methyl Ester

The title compound was prepared as described in Example 6a by substituting 2-(chloromethyl)quinoline for 4-(chloromethyl)quinoline. The product (38.1 g, 130 mmol) was obtained in 65% yield after recrystallization from methylene chloride-ether-hexane, m.p. 82°–85° C.

1H NMR (CDCl3, 400 MHz) δ: 8.22 (d, J=8.5 Hz, 1H), 8.06 (d, J=8.4 Hz, 1H), 7.93 (d, J=8.5 Hz, 1H), 7.87 (dd, J=7.8, 1.8 Hz, 1H), 7.83 (dd, J=8.2, 1.1 Hz, 1H), 7.73 (ddd, J=8.3, 6.9, 1.4 Hz, 1H), 7.54 (ddd, J=8.0, 6.9, 1.1 Hz, 1H), 7.43 (ddd, J=8.4, 7.4, 1.8 Hz, 1H), 7.06 (dd, J=8.4, 0.4 Hz, 1H), 7.01 (td, J=7.5, 1.0 Hz, 1H), 5.47 (s, 2H), 3.95 (s, 3H)

MS(EI), m/z (rel. intensity)=293 (M+, 11), 158 (17), 142 (100), 115 (36)

IR (Kbr) ν: 3440, 3040, 1725, 1600, 1580, 1440, 1420, 1250, 1090, 830, 740 cm−1

Anal. Calcd. for C18H15NO3: C, 73.71; H, 5.15; N, 4.78. Found: C, 73.50; H, 5.20; N, 4.73.

Step b) Preparation of 2-(2-Quinolinylmethoxy)benzoic Acid 2-(2-Quinolinylmethoxy)benzoic acid methyl ester (29.32 g, 100 mmol) and 2.5N NaOH (aq) (80 mL, 200 mmol) were refluxed for 1 hour in MeOH (250 mL). The dark yellow solution was treated three times with activated charcoal (13 g), then neutralized with conc. HCl (16.5 mL, 200 mmol). Filtration of the chilled precipitate afforded two crops of the free acid, 24 g (86 mmol, 86% yield), as a pink solid. An analytical sample was prepared by recrystallization from acetonitrile, m.p. 164°–166° C. (dec).

1H NMR (DMSO-d6, 400 MHz) δ: 13.0 (s, 1H), 8.42 (d, J=8.5 Hz, 1H), 8.00 (d, J=8.4 Hz, 1H), 7.98 (d, J=8.4 Hz, 1H), 7.80 (d, J=8.4 Hz, 1H), 7.78 (ddd, J=8.4, 6.9, 1.5 Hz, 1H), 7.71 (dd, J=7.6, 1.8 Hz, 1H), 7.61 (ddd, J=8.0, 6.9, 1.1 Hz, 1H), 7.48 (ddd, J=8.4 7.4, 1.8 Hz, 1H), 7.25 (d, J=8.4 Hz, 1H), 7.03 (td, J=7.5, 0.9 Hz, 1H), 5.49 (s, 2H);

MS(EI), m/z (rel. intensity)=279 (M+, 1), 235 (30), 234 (20), 158 (24), 142 (100)

IR (KBr) v: 3420, 1710, 1600, 1490, 1450, 1250, 1085, 830, 750 cm$^{-1}$

Anal. Calcd. for $C_{17}H_{13}NO_3$: C, 73.11; H, 4.69; N, 5.01. Found: C, 73.47; H, 4.61; N, 5.14.

Step c) Preparation of N-[1-(Phenylmethyl)-4-piperidinyl)-2-(2-quinolinylmethoxy)benzamide The title compund was prepared as described in Example 4 by substituting 2-(2-quinolinylmethoxy)benzoic acid for 4-(2-quinolinylmethoxy)benzoic acid sodium salt and 4-amino-1-benzylpiperidine for 4-amino-1-butylpiperindine. The dried product (3.36 g, 7.44 mmol) was obtained in 75% yield after recrystallization from ether-hexane and acetonitrile, m.p. 138°-140° C.

$^1$H NMR (CDCl$_3$, 400 MHz) δ: 8.24 (d, J=8.5 Hz, 1H), 8.22 (dd, J=7.9, 1.8 Hz, 1H), 8.17 (d, J=8.5 Hz, 1H), 8.05 (d, J=7.6 Hz, 1H), 7.86 (d, J=8.1 Hz, 1H), 7.78 (ddd, J=8.3, 6.9, 1.4 Hz, 1H), 7.60 (ddd, J=8.0, 7.0, 1.0 Hz, 1H), 7.55 (d, J=8.5 Hz, 1H), 7.41 (ddd, J=7.9, 7.5 1.8 Hz, 1H), 7.26 (m, 5H), 7.10 (t, J=7.5 Hz, 1H), 7.07 (d, J=7.9 Hz, 1H), 5.48 (s, 2H), 4.05 (m, 1H), 3.40 (s, 2H), 2.64 (br, 2H), 2.11 (td, J=11.5, 2.3 Hz, 2H), 1.93 (dd, J=12.8,. 3.5 Hz, 2H), 1.47 (qd, J=12.8, 3.5 Hz, 2H)

MS(CI), m/z (rel. intensity)=452 (MH$^+$, 10), 367 (10), 353 (8), 311 (100), 144 (75)

IR (KBr) v: 3320, 2960, 1630, 1605, 1535, 1250, 750 cm$^{-1}$

Anal. Calcd. for $C_{29}H_{29}N_3O_2$: C, 77.13; H, 6.47; N, 9.30. Found: C, 76.83, 11, 6.42; N, 9.20.

EXAMPLE 9

N-(1-Butyl-4-piperidinyl)-3-(4-quinolinylmethoxy)benzamide 3-(4-Quinolinylmethoxy)benzoyl chloride hydrochloride (2.34 g, 7.0 mmol) of Example 5b was treated with 4-amino-1-butylpiperidine (1.64 g, 10.5 mmol) in methylene chloride. After 0.5 hour, the filtered reaction was extracted with 1N NaOH (aq) (2×75 mL) and water (2×100 mL). Evaporation of the dried (MgSO$_4$) organic phase afforded, after crystallization from acetonitrile and drying in vacuo overnight, 1.9 g (4.5 mmol, 65% yield) of the product as a yellow solid, m.p. 147°-149° C.

$^1$H NMR (CDCl$_3$, 400 MHz) δ: 8.91 (d, J=4.4 Hz, 1H), 8.17 (d, J=8.4 Hz, 1H), 7.98 (dd, J=8.4, 0.8 Hz, 1H), 7.76 (ddd, J=8.3, 6.9, 1.4 Hz, 1H), 7.61 (ddd, J=8.1, 6.9, 1.2 Hz, 1H), 7.57 (d, J=4.4 Hz, 1H), 7.53 (dd, J=2.4, 1.5 Hz, 1H), 7.37 (t, J=7.7 Hz, 1H), 7.32 (dt, J-7.7, 1.3 Hz, 1H), 7.13 (ddd, J=8.0, 2.6, 1.1 Hz, 1H), 6.03 (d, J=7.8 Hz, 1H), 5.58 (s, 2H), 4.00 (m, 1H), 2.88 (d, J=11.7 Hz, 2H), 2.33 (t, J=7.6 Hz, 2H), 2.12 (t, J=11.5 Hz, 2H), 2.04 (dd, J=12.1, 1.5 Hz, 2H), 1.56 (qd, J=12.1, 3.7 Hz, 2H), 1.48 (p, J=7.5 Hz, 2H), 1.32 (sextet, J=7.3 Hz, 2H), 0.92 (t, J=7.3 Hz, 3H)

MS(CI), m/z (rel. intensity) 418 (MH$^+$, 100), 277 (60)

IR (KBr) v: 3440, 3280, 2930, 1635, 1600, 1590, 1540, 1340, 1310, 1255, 1240, 870, 840, 750 cm$^{-1}$

Anal. Calcd. for $C_{26}H_{31}N_3O_2$: C, 74.79; H, 7.48; N, 10.06. Found: C, 74.74; H, 7.49; N, 10.06.

EXAMPLE 10

N-[1-(Phenylmethyl)-4-piperidinyl]-4-(1-naphthalenylmethoxy)benzamide

Step a) Preparation of 4-(1-Naphthalenylmethoxy)benzoic Acid Methyl Ester

A mixture of methyl 4-hydroxybenzoate (30.42 g, 200 mmol), cesium carbonate (65.16 g, 200 mmol), potassium iodide (6.64 g, 40 mmol), and 1-(chloromethyl)-naphthalene (45.93 g, 260 mmol) was suspended in acetone (700 mL) and refluxed for 5 hours. After removal of the solvent in vacuo, the residue was suspended in methylene chloride and extracted sequentially with water (1×300 mL), 1N NaOH (aq) (2×300 mL), and water (2×300 mL). The dried (MgSO$_4$) organic phase was evaporated to a residue and crystallized from methylene chloride-ether (minimum)-hexane to afford 56.4 g (193 mmol, 97% yield) of the product as an off-white solid. An analytical sample was prepared by flash column chromatography on silica gel (75:1 loading ratio, CH$_2$Cl$_2$ eluant) and recrystallization from methylene chloride-ether (minimum)-hexane, m.p. 84°-86° C.

$^1$H NMR (CDCl$_3$, 400 MHz) δ: 8.04 (d, J=9.0 Hz, 2H), 8.03 (m, 1H), 7.91 (dd, J=5.9, 2.4 Hz, 1H), 7.88 (d, J=8.4 Hz, 1H), 7.60 (d, J=6.9 Hz, 1H), 7.55 (m, 2H), 7.48 (dd, J=8.2, 7.0 Hz, 1H), 7.08 (d, J=8.9 Hz, 2H), 5.55 (s, 2H), 3.90 (s, 3H)

MS(EI), m/z (rel. intensity)=292 (M$^+$, 10), 141 (100), 115 (20)

IR (KBr) v: 3440, 3060, 2960, 1715, 1615, 1520, 1440, 1290, 1270, 1180, 1120, 1070, 1005, 850, 790, 730 cm$^{-1}$

Anal. Calcd. for $C_{19}H_{16}O_3$: C, 78.06; H, 5.52. Found: C, 77.75; H, 5.34.

Step b) Preparation of 4-(1-Naphthalenylmethoxy)benzoic Acid Sodium Salt 4-(1-Naphthalenylmethoxy)benzoic acid methyl ester (5.47 g, 18.7 mmol) and 2.5N NaOH (aq) (40 mL, 100 mmol) were refluxed for 2 hours in methanol (250 mL). The volume was reduced, water added, and after cooling and filtration afforded 3.52 g (11.7 mmol, 63% yield) of the sodium salt which was dried in vacuo overnight (6 hours at 120° C.), m.p. >360° C.

$^1$H NMR (DMSO-d$_6$, 400 MHz) δ: 8.08 (dd, J=6.9 Hz, 2.2 Hz, 1H), 7.95 (dd, J=6.9 Hz, 2.5 Hz, 1H), 7.92 (d, J=8.1 Hz, 1H), 7.91 (d, J=8.7 Hz, 2H), 7.66 (d, J=6.8 Hz, 1H), 7.55 (m, 2H), 7.49 (dd, J=8.1, 7.2 Hz, 1H), 6.99 (d, J=8.8 Hz, 2H), 5.54 (s, 2H)

MS(−FSB), m/z (rel. intensity)=277 (M$^-$, 50)

IR (KBr) v: 3420, 3040, 1590, 1545, 1420, 1250, 1005, 790, 780, 770 cm$^{-1}$

Karl Fisher, 0.48% H$_2$O

Anal. Calcd. for $C_{18}H_{13}NaO_3$: C, 72.00; H, 4.36. Found: C, 71.21; H, 4.28.

Step c) Preparation of 4-(1-Naphthalenylmethoxy)benzoic Acid 4-(1-Naphthalenylmethoxy)benzoic acid methyl ester (26.3 g, 90 mmol) and 2.5N NaOH (aq) (180 mL, 450 mmol) were refluxed for 3 hours in methanol (250 mL). Neutralization with conc. HCl (37.2 mL, 450 mmol) and addition of water afforded, after filtration of the chilled precipitate, 14.8 g (53 mmol, 59% yield) of the free acid as a white solid.

Step d) Preparation of N-[1-(Phenylmethyl)-4-piperidinyl]-4-(1-naphthalenylmethoxy)benzamide A mixture of 4-(1-naphthalenylmethoxy)benzoic acid (3.8 g, 13.67 mmol), 1-(3-dimethylamino-propyl)-3-ethylcarbodiimide hydrochloride (4.02 g, 21.0 mmol), and 1-hydroxybenzotriazole monohydrate (2.3 g, 17.0 mmol) were stirred in methylene chloride (150 mL) and dry DMF (15 mL) for 2 hours at room temperature under nitrogen, then treated dropwise with a solution of 4-amino-1-benzylpiperidine (2.60 g, 13.67 mmol) and triethylamine (4.15 g, 41.0 mmol) in methylene chloride. After 2 hours the reaction mixture was extracted sequentially with 1N NaOH (2×100 mL), water (3×200 mL), 0.1N HCl (425 mL, 42.5 mmol), water, 1N NaOH (aq), and water. The dried (MgSO$_4$) organic phase was evaporated to a residue and crystallized from methylene chloride-ether, (5.4 g, 12.0 mmol, 88%). The product was purified by flash column chromatography on silica gel (100:1 loading ratio; $CH_2Cl_2$/MeOH, 95/5 (eluant), and recrystallization from methylene chloride-ether afforded 4.66 g (10.3 mmol, 76% yield) as a white solid, m.p. 173°-175° C.

$^1$H NMR ($CDCl_3$, 400 MHz) δ: 8.01 (dd, J=6.8, 2.5 Hz, 1H), 7.90 (dd, J=6.9, 2.5 Hz, 1H), 7.86 (d, J=8.2 Hz, 1H), 7.73 (d, J=8.9 Hz, 2H), 7.58 (d, J=6.9 Hz, 1H), 7.53 (m, 2H), 7.46 (dd, J=8.2, 7.1 Hz, 1H), 7.32 (m, 4H), 7.26 (m, 1H), 7.06 (d, J=8.8 Hz, 2H), 5.88 (d, J=7.9 Hz, 1H), 5.53 (s, 2H), 4.00 (m, 1H), 3.51 (s, 2H), 2.85 (d, J=11.8 Hz, 2H), 2.17 (td, J=11.3, 1.6 Hz, 2H), 2.01 (dd, J=12.5, 3.3 Hz, 2H), 1.54 (qd, J=11.2, 3.7 Hz, 2H)

MS(EI), m/z (rel. intensity)=450 (M+, 50), 173 (30), 141 (100), 91 (50)

IR (KBr) ν: 3440, 3220, 2950, 1625, 1605, 1505, 1330, 1230, 1180, 1005, 805, 730 cm$^{-1}$

Anal. Calcd. for $C_{30}H_{30}N_2O_2$: C, 79.97; H, 6.71; N, 6.22. Found: C, 79.99; H, 6.75; N, 6.15.

EXAMPLE 11

N-(1-Butyl-4-piperidinyl)-4-(1-naphthalenylmethoxy)-benzamide

The title compound was prepared as described in Example 10d by substituting 4-amino-1-butylpiperidine for 4-amino-1-benzylpiperidine. Recrystallization from methylene chloride-ether and drying in vacuo (6 hours at 80° C.) overnight afforded 3.1 g (7.4 mmol, 50% yield) of the product as a white solid, m.p. 173.5°-175° C.

$^1$H NMR ($CDCl_3$, 400 MHz) δ: 8.01 (dd, J=6.7, 2.4 Hz, 1H), 7.90 (dd, J=7.0, 2.5 Hz, 1H), 7.86 (d, J=8.2 Hz, 1H), 7.73 (d, J=8.8 Hz, 2H), 7.58 (d, J=6.7 Hz, 1H), 7.53 (m, 2H), 7.46 (dd, J=8.2, 7.2 Hz, 1H), 7.06 (d, J=8.8 Hz, 2H), 5.86 (d, J=7.8 Hz, 1H), 5.53 (s, 2H), 3.99 (m, 1H), 2.88 (d, J=11.6 Hz, 2H), 2.33 (t, J=7.6 Hz, 2H), 2.11 (t, J=11.5 Hz, 2H), 2.03 (dd, J=12.2, 2.6 Hz, 2H), 1.54 (qd, J=11.4, 3.6 Hz, 2H), 1.47 (p, J=7.5 Hz, 2H), 1.32 (sextet, J=7.4 Hz, 2H), 0.91 (t, J=7.3 Hz, 3H)

MS(EI), m/z (rel. intensity)=416 (M+, 40), 373 (100), 141 (45)

IR (KBr) ν: 3210, 2920, 1625, 1605, 1530, 1500, 1230, 1175, 1000, 840, 785, 765 cm$^{-1}$

Anal. Calcd. for $C_{27}H_{32}N_2O_2$: C, 77.85; H, 7.74; N, 6.73. Found: C, 78.18; H, 7.76; N, 6.68.

EXAMPLE 12

(E)-N-[1-(Phenylmethyl)-4-piperidinyl]-4-[2-(4-quinolinyl)ethenyl]benzamide

Step a) Preparation of (E) and (Z)-4-[2-(4-Quinolinyl)ethenyl]benzoic Acid Methyl Ester A stirred mixture of 4-quinolinecarboxaldehyde (7.85 g, 50 mmol) and [[(4-carboxy)phenyl]methyl]triphenylphosphonium chloride (21.64 g, 50 mmol) in 100 mL of dry DMF was treated with triethylamine (5.05 g, 50 mmol) at 45° C. for 0.5 hour. The reaction was further treated with potassium carbonate (6.91 g, 50 mmol) and dimethylsulfate (6.30 g, 50 mmol) and stirred at 50° C. under nitrogen for 1 hour. The mixture was poured into water and extracted with methylene chloride (3×300 mL). The combined organic phase was washed with water (2×200 mL), dried ($MgSO_4$), and evaporated in vacuo to a residue, which, after recrystallization from methylene chloride-ether and acetonitrile, afforded 2.1 g (7.3 mmol, 15% yield) of the E isomer as white needles. The combined filtrates were evaporated in vacuo and purified by preparative HPLC to afford 2.45 g (8.5 mmol, 17% yield) of the Z isomer as a clear oil.

(E isomer), m.p. 154°-156° C.

$^1$H NMR ($CDCl_3$, 400 MHz) δ: 8.92 (d, J=4.6 Hz, 1H), 8.21 (d, J=8.4 Hz, 1H), 8.15 (d, J=8.4 Hz, 1H), 8.10 (d, J=8.4 Hz, 2H), 7.92 (d, J=16.1 Hz, 1H), 7.75 (ddd, J=8.2, 6.9, 1.3 Hz, 1H), 7.68 (d, J=8.4 Hz, 2H), 7.61 (ddd, J=8.1, 6.9, 1.2 Hz, 1H), 7.60 (d, J=4.6 Hz, 1H), 7.35 (d, J=16.1 Hz, 1H), 3.95 (s, 3H)

MS(EI), m/z (rel. intensity)=289 (M+, 25), 230 (100), 202 (35), 115 (60), 101 (82)

IR (KBr) ν: 3420, 1705, 1595, 1570, 1270, 1185, 1170, 1100, 740 cm$^{-1}$

Anal. Calcd. for $C_{19}H_{15}NO_2$: C, 78.87; H, 5.23; N, 4.84. Found: C, 78.76; H, 5.16; N, 4.63

(Z isomer), oil $^1$H NMR ($CDCl_3$, 400 MHz) δ: 8.76 (d, J=4.4 Hz, 1H), 8.15 (d, J=8.4 Hz, 1H), 8.02 (dd, J32 8.4, 0.8 Hz, 1H), 7.78 (d, J=8.4 Hz, 2H), 7.74 (ddd, J=8.3, 6.9, 1.4 Hz, 1H), 7.54 (ddd, J=8.1, 6.9, 1.2 Hz, 1H), 7.18 (dd, J=4.4, 0.8 Hz, 1H), 7.12 (d, J=8.4 Hz, 2H), 7.09 (dd, J=12.4, 0.7 Hz, 1H), 7.00 (d, J=12.4 Hz, 1H), 3.85 (s, 3H)

MS(+FAB), m/z (rel. intensity)=290 (MH+, 100)

IR (KBr) ν: 3400, 2940, 1715, 1600, 1580, 1430, 1275, 1100, 1010, 890, 850, 760, 690 cm$^{-1}$

Anal. Calcd. for $C_{19}H_{15}NO_2$: C, 78.87; H, 5.23; N, 4.84. Found: C, 77.53; H, 5.07; N, 5.14.

Step b) Preparation of (E)-4-[2-(4-Quinolinyl)ethenyl]benzoic Acid (E)-4-[2-(4-Quinolinyl)ethenyl]benzoic acid methyl ester (1.7 g, 5.9 mmol) and 2.5N NaOH (aq) (12 mL, 30 mmol) were refluxed for 6 hours in MeOH (50 mL). Neutralization at reflux with conc. HCl (2.5 mL, 30 mmol) and filtration of the cooled precipitate afforded 1.58 g (5.7 mmol, 98% yield) of the free acid as a white solid, m.p.>360° C.

$^1$H NMR (DMSO-$d_6$, 400 MHz) δ:12.95 (br s, 1H), 8.91 (d, J=4.6 Hz, 1H), 8.54 (ddd, J=8.01, 1.4, 0.4 Hz, 1H), 8.23 (dd, J=16.2, 0.4 Hz, 1H), 8.03 (d, J=8.5 Hz, 1H), 8.00 (d, J=8.3 Hz, 2H), 7.95 (d, J=8.1 Hz, 2H), 7.88 (br, d, J=1.0 Hz, 1H), 7.80 (ddd, J=8.0, 6.8, 1.2 Hz, 1H), 7.67 (ddd, J=8.0, 6.8, 1.2 Hz, 1H), 7.65 (d, J=16.2 Hz, 1H)

MS (−FAB), m/z (rel. intensity)=274 (M−40), 148 (100)

IR (KBr) ν: 3420, 2400, 1940, 1690, 1600, 1575, 1500, 1260, 1230, 1170, 950, 755, 730 cm$^{-1}$

Anal. Calcd. for $C_{18}H_{13}NO_2$: C, 78.53; H, 4.76; N, 5.09. Found: C, 78.45; H, 4.70; N, 5.22.

Step c) Preparation of (E)-N-[1-(Phenylmethyl)-4-piperidinyl]-4-[2-(4-quinolinyl)ethenyl]benzamide A mixture of (E)-4-[2-(4-quinolinyl)ethenyl]benzoic acid (1.35 g, 4.9 mmol), 1-(3-dimethylaminopropyl)-3-ethylcarbodiimide hydrochloride (2.86 g, 15.0 mmol), and 1-hydroxybenzotriazole monohydrate (1.69 g, 12.5 mmol) was stirred in methylene chloride (100 mL) and dry DMF (50 mL) for 1 hour at 45° C. under nitrogen; then treated dropwise with a solution of 4-amino-1-benzylpiperidine (0.95 g, 5.0 mmol) and triethylamine (3.04 g, 30 mmol) in methylene chloride. After 1 hour at 45° C. the reaction mixture was extracted with 1N NaOH (200 mL) and water (3×200 mL). The dried ($MgSO_4$) organic phase was evaporated to a residue, which, after recrystallization from methylene chloride-acetonitrile and drying in vacuo overnight (4 hours at 90° C.) afforded 0.78 g (1.7 mmol, 36% yield) of the product as a white solid, m.p. 188°–190° C.

$^1$H NMR (CDCl$_3$, 400 MHz) δ: 8.90 (d, J=4.6 Hz, 1H), 8.19 (dd, J=8.5, 0.8 Hz, 1H), 8.14 (dd, J=8.5, 0.8 Hz, 1H), 7.86 (d, J=16.0 Hz, 1H), 7.81 (d, J=8.3 Hz, 2H), 7.74 (ddd, J=8.0, 6.8, 1.2 Hz, 1H), 7.65 (d, J=8.3 Hz, 2H), 7.59 (ddd, J=8.0, 6.8, 1.2 Hz, 1H), 7.58 (d, J=4.4 Hz, 1H), 7.33 (d, J=16.2 Hz, 1H), 7.32 (m, 4H), 7.26 (m, 1H), 6.13 (d, J=7.9 Hz, 1H), 4.03 (m, 1H), 3.52 (s, 2H), 2.86 (dd, J=12.0, 3.1 Hz, 2H), 2.18 (td, J=11.6, 1.9 Hz, 2H), 2.05 (d, J=12.4 Hz, 2H), 1.59 (qd, J=11.2, 3.7 Hz, 2H)

MS(+FAB), m/z (rel. intensity)=448 (MH+, 20), 237 (30), 91 (100)

IR (KBr) v: 3280, 2930, 2780, 1625, 1540, 1500, 1335, 1100, 1060, 960, 750, 740, 700 cm$^{-1}$

Anal. Calcd. for C$_{30}$H$_{29}$N$_3$O: C, 80.51; H, 6.53; N, 9.39. Found: C, 79.07; H, 6.46; N, 9.52.

EXAMPLE 13

(Z)-N-[1-(Phenylmethyl)-4-piperidinyl]-4-[2-(4-quinolinyl)ethenyl]benzamide

Step a) Preparation of (Z)-4-[2-(4-Quinolinyl)ethenyl]benzoic Acid

The title compound was prepared as described in Example 12b by substituting (Z)-4-[2-(4-quinolinyl)ethenyl]benzoic acid methyl ester for (E)-4-[2-(4-quinolinyl)ethenyl]benzoic acid methyl ester. Crystallization from methanol-water afforded the free acid (1.45 g, 5.3 mmol) in 72% yield, m.p. 222°–225° C.

$^1$H NMR (DMSO-d$_6$, 400 MHz) δ: 12.9 (s, 1H), 8.77 (d, J=7.44 Hz, 1H), 8.05 (d, J=8.5 Hz, 1H), 8.03 (dd, J=8.7, 0.9 Hz, 1H), 7.77 (ddd, J=8.3 6.9, 1.4 Hz, 1H), 7.70 (d, J=8.4 Hz, 2H), 7.59 (ddd, J=8.1, 6.9, 1.2 Hz, 1H), 7.24 (dd, J=4.4, 0.9 Hz, 1H), 7.22 (d, J=12.6 Hz, 1H), 7.14 (d, J=8.4 Hz, 2H), 7.11 (d, J=12.6 Hz, 1H)

MS(EI), m/z (rel. intensity)=275 (M+, 100) 230 (90)

IR (KBr) v: 3420, 2360, 1920, 1705, 1610, 1590, 1280, 1250, 870, 770 cm$^{-1}$

Anal. Calcd. for C$_{18}$H$_{13}$NO$_2$: C, 78.53; H, 4.76; N, 5.09. Found: C, 78.34; H, 4.64; N, 4.99.

Step b) Preparation of (Z)-N-[1-(Phenylmethyl)-4-piperidinyl]-4-[2-(4-quinolinyl)ethenyl]benzamide The title compound was prepared as described in Example 12c by substituting (Z)-4-[2-(4-quinolinyl)ethenyl]benzoic acid for (E)-4-[2-(4-quinolinyl)ethenyl]benzoic acid. Crystallization from methylene chloride-ether afforded the product (1.45 g, 3.2 mmol) as a white solid in 81% yield, m.p. 139°–141° C.

$^1$H NMR (CDCl$_3$, 400 MHz) δ: 8.75 (d, J=4.4 Hz, 1H), 8.13 (dd, J=8.5, 0.6 Hz, 1H), 8.02 (dddd, J=8.3, 1.2, 0.8, 0.6 Hz, 1H), 7.73 (ddd, J=8.0, 6.8, 1.2 Hz, 1H), 7.53 (ddd, J=8.0, 6.8, 1.2 Hz, 1H), 7.48 (d, J=8.3 Hz, 2H), 7.29 (m, 4H), 7.25 (m, 1H), 7.16 (dd, J=4.4, 0.8 Hz, 1H), 7.09 (d, J=8.3 Hz, 2H), 7.06 (dd, J=12.4, 0.6 Hz, 1H), 6.97 (d, J=12.4 Hz, 1H), 5.86 (d, J=7.9 Hz, 1H), 3.94 (m, 1H), 3.48 (s, 2H), 2.80 (d, J=11.8 Hz, 2H), 2.13 (dd, J=11.8, 2.1 Hz, 2H), 1.95 (dtd, J=10.6, 2.1, 1.7 Hz, 2H), 1.48 (qd, J=11.4, 3.9 Hz, 2H)

MS(CI), m/z (rel. intensity)=448 (MH+, 30), 259 (35), 107 (40), 80 (100)

IR (KBr) v: 3420, 3210, 3050, 2940, 2790, 1620, 1495, 1330, 1065, 850, 755, 725, 690 cm$^{-1}$

Anal. Calcd. for C$_{30}$H$_{29}$N$_3$O: C, 80.51; H, 6.53; N, 9.39. Found: C, 80.22; H, 6.54; N, 9.42.

EXAMPLE 14

N-[1-(Phenylmethyl)-4-piperidinyl]-4-(4-quinolinylmethoxy)benzamide N-Oxide

Step a) Preparation of 4-(4-Quinolinylmethoxy)benzoic Acid Methyl Ester N-Oxide

A stirred methylene chloride solution of 4-(4-quinolinylmethoxy)benzoic acid methyl ester (2.93 g, 10 mmol) was treated at room temperature with 3-chloroperoxybenzoic acid (3.23 g, 15 mmol) in two aliquots. After 2 hours, the reaction mixture was extracted with 1N NaOH (aq) (2×100 mL) and water (2×100 mL). The dried (MgSO$_4$) organic phase was evaporated to a residue and recrystallized from acetonitrile to afford, after drying in vacuo overnight (6 hours at 90° C.), 2.4 g (7.8 mmol, 78% yield) of the N-oxide as a white solid, m.p. 171°–173° C.

$^1$H NMR (CDCl$_3$, 400 MHz) δ: 8.84 (d, J=8.8 Hz, 1H), 8.53 (d, J=6.2 Hz, 1H), 8.05 (d, J=8.9 Hz, 2H), 8.01 (d, J=8.4 Hz, 1H), 7.82 (ddd, J=8.1, 6.9, 1.2 Hz, 1H), 7.73 (ddd, J=8.2, 7.0, 1.2 Hz, 1H), 7.45 (d, J=6.2 Hz, 1H), 7.06 (d, J=8.9 Hz, 2H), 5.51 (s, 2H), 3.90 (s, 3H)

MS(EI), m/z (rel. intensity)=309 (M+, 20), 293 (20), 158 (100), 142 (30)

IR (KBr) v: 2980, 2940, 1705, 1605, 1510, 1440, 1310, 1280, 1260, 1170, 1050, 825, 760, 750 cm$^{-1}$

Anal. Calcd. for C$_{18}$H$_{15}$NO$_4$: C, 69.89; H, 4.89; N, 4.53. Found: C, 70.06; H, 4.89; N, 4.33.

Step b) Preparation of 4-(4-Quinolinylmethoxy)benzoic Acid N-Oxide

The title compound was prepared as described in Example 12b by substituting 4-(4-quinolinylmethoxy)benzoic acid methyl ester N-oxide for (E)-4-[2-(4-quinolinyl)ethenyl]benzoic acid methyl ester. Crystallization from methanol-water afforded the free acid (1.8 g, 6.1 mmol) in 99% yield, after drying in vacuo overnight (6 hours at 90° C.), m.p. 232°–233° C. (dec).

$^1$H NMR (DMSO-d$_6$, 400 MHz) δ: 12.7 (s, 1H), 8.60 (d, J=6.3 Hz, 2H), 8.21 (d, J=8.1 Hz, 1H), 7.92 (d, J=8.8 Hz, 2H), 7.86 (ddd, J=8.2, 7.0, 1.2 Hz, 1H), 7.79 (ddd, J=8.3, 7.0, 1.3 Hz, 1H), 7.60 (d, J=6.2 Hz, 1H), 7.20 (d, J=8.8 Hz, 2H), 5.64 (s, 2H)

MS(EI), m/z (rel. intensity) 295 (M+, 10), 279 (10), 158 (100), 142 (30)

IR (KBr) v: 3420, 3060, 3010, 2400, 1850, 1675, 1600, 1505, 1290, 1230, 1200, 1160, 1140, 1050, 1000, 765, 750, 650 cm$^{-1}$

Anal. Calcd. for C$_{17}$H$_{13}$NO$_4$: C, 69.15; H, 4.44; N, 4.74. Found: C, 69.07; H, 4.15; N, 4.66.

Step c) Preparation of N-[1-(Phenylmethyl)-4-piperidinyl]-4-(4-quinolinylmethoxy)benzamide N-Oxide The title compound was prepared as described in Example 12c by substituting 4-(4-quinolinylmethoxy)benzoic acid N-oxide for (E)-4-[2-(4-quinolinyl)ethenyl]benzoic acid. Recrystallization from methylene chloride-ether and methylene chloride-methanol afforded the product (1.34 g, 2.9 mmol) as a white solid in 72% yield, m.p. 223°–225° C. (dec).

$^1$H NMR (CDCl$_3$+3d DMSO-d$_6$, 400 MHz) δ: 8.60 (d, J=8.5 Hz, 1H), 8.31 (d, J=6.2 Hz, 1H), 7.86 (dd, J=8.3, 0.4 Hz, 1H), 7.63 (d, J=8.7 Hz, 2H), 7.62 (ddd, J=8.3, 7.3, 1.0 Hz, 1H), 7.53 (ddd, J=8.3, 7.3, 1.0 Hz, 1H), 7.29 (d, J=6.2 Hz, 1H), 7.12 (m, 4H), 7.05 (m, 1H), 6.85 (d, J=8.7 Hz, 2H), 6.67 (d, J=7.9 Hz, 1H), 5.31 (s, 2H), 3.78 (m, 1H), 3.31 (s, 2H), 2.67 (d, J=11.8 Hz, 2H), 1.95 (t, J=10.4 Hz, 2H), 1.76 (d, J=10.6 Hz, 2H), 1.42 (qd, J=11.5, 3.5 Hz, 2H)

MS(+FAB), m/z (rel. intensity)=468 (MH+, 75), 452 (25), 91 (100)

IR (KBr) v: 3280, 1680, 1601, 1501, 1230 cm$^{-1}$

Anal. Calcd. for $C_{29}H_{29}N_3O_3$: C, 74.50; H, 6.25; N, 8.99. Found: C, 74.34; H, 6.23; N, 9.02.

EXAMPLE 15

N-[1-[[4-[(Diethylamino)carbonyl]phenyl]methyl]-4-piperidinyl]-4-(4-quinolinylmethoxy)benzamide A mixture of 4-(4-quinolinylmethoxy)benzoic acid (0.98 g, 3.5 mmol), 1-(3-dimethylaminopropyl)-3-ethylcarbodiimide hydrochloride (1.15 g, 6 mmol), and 1-hydroxybenzotriazole monohydrate (0.68 g, 5.0 mmol) were stirred in methylene chloride (50 mL) and dry DMF (5 mL) for 2 hours under nitrogen, then treated with 4-[(4-amino-1-piperidinyl)methyl]-N,N-diethylbenzamide (1.01 g, 3.5 mmol) and triethylamine (1.82 g, 18 mmol) in methylene chloride. After 1 hour, the reaction mixture was extracted with 1N NaOH (25 mL) and water (3×50 mL). The dried (MgSO$_4$) organic phase was evaporated to a residue, which, after recrystallization from acetonitrile and drying in vacuo overnight (6 hours at 90° C.), afforded 1.2 g (2.2 mmol, 62% yield) of the product as a white solid, m.p. 189°–191° C.

$^1$H NMR (CDCl$_3$, 400 MHz, mixture of rotamers) δ: 8.92 (d, J=4.4 Hz, 1H), 8.18 (d, J=7.9 Hz, 1H), 7.98 (dd, J=8.4, 0.7 Hz, 1H), 7.77 (ddd, J=8.2, 6.9 1.3 Hz, 1H), 7.75 (d, J=8.9 Hz, 2H), 7.63 (ddd, J=8.2, 6.9, 1.3 Hz, 1H), 7.55 (d, J=4.4 Hz, 1H), 7.34 (d, J=6.0 Hz, 2H), 7.33 (d, J=6.0 Hz, 2H), 7.05 (d, J=8.9 Hz, 2H), 5.96 (d, J=7.9 Hz, 1H), 5.60 (s, 2H), 4.00 (m, 1H), 3.53 (br s, 2H), 3.52 (s, 2H), 3.27 (br s, 2H), 2.84 (d, J=11.7 Hz, 2H), 2.18 (t, J=11.4 Hz, 2H), 2.01 (d, J=9.6 Hz, 2H), 1.54 (qd, J=11.9, 3.6 Hz, 2H), 1.24 (br s, 3H), 1.12 (br s, 3H)

MS(+FAB), m/z (rel. intensity)=551 (MH+, 60), 410 (20), 271 (20), 190 (50), 143 (40), 116 (50), 91 (100)

IR (KBr) v: 3420, 3240, 2920, 2740, 1620, 1495, 1250, 1230, 840, 750 cm$^{-1}$

Anal. Calcd. for $C_{34}H_{38}N_4O_3$: C, 74.16; H, 6.96; N, 10.17. Found: C, 74.27; H, 6.88; N, 9.99.

EXAMPLE 16

1-(Phenylmethyl)-N-[[4-(4-quinolinylmethoxy)phenyl]methyl]-4-piperidinamine

Step a) Preparation of 4-(4-Quinolinylmethoxy)benzaldehyde

A mixture of 4-hydroxybenzaldehyde (6.1 g, 50 mmol), cesium carbonate (32.6 g, 100 mmol), potassium iodide (1.66 g, 10 mmol), and 4-(chloromethyl)quinoline hydrochloride (10.71 g, 50 mmol) was suspended in acetone (600 mL) and refluxed for 8 hours. After 54 hours at room temperature, the solvent was removed in vacuo, the residue was suspended in methylene chloride and extracted sequentially with water (100 mL), 1N NaOH (aq) (2×100 mL), and water (2×100 mL). The dried (MgSO$_4$) organic phase was evaporated to a residue which afforded, after repeated recrystallization from methylene chloride-ether-hexane and drying in vacuo overnight (6 hours at 90° C.), 4.25 g (16.1 mmol, 32% yield) of the aldehyde as a white solid, m.p. 134°–136° C.

$^1$H NMR (CDCl$_3$, 400 MHz) δ: 9.92 (s, 1H), 8.94 (d, J=4.4 Hz, 1H), 8.20 (d, J=8.5 Hz, 1H), 7.98 (dd, J=8.4, 0.8 Hz, 1H), 7.88 (d, J=8.8 Hz, 2H), 7.79 (ddd, J=8.3, 6.9, 1.4 Hz, 1H), 7.64 (ddd, J=8.2, 6.9, 1.3 Hz, 1H), 7.55 (d, J=4.4 Hz, 1H), 7.15 (d, J=8.7 Hz, 2H), 5.65 (s, 2H)

MS(EI), m/z (rel. intensity)=263 (M+, 13), 142 (100)

IR (KBr) v: 3400, 1685, 1580, 1565, 1490, 1440, 1240, 1140, 840, 830, 740 cm$^{-1}$

Anal. Calcd. for $C_{17}H_{13}NO_2$: C, 77.55; H, 4.98; N, 5.32. Found: C, 77.77; H, 5.01; N, 5.34.

Step b) Preparation of 1-(Phenylmethyl)-N-[[4-(4-quinolinylmethoxy)phenyl]methyl]-4-piperidinamine A mixture of 4-(4-quinolinylmethoxy)benzaldehyde (2.63 g, 10 mmol), 4-amino-1-benzylpiperidine (2.5 g, 13.1 mmol), and 4-toluenesulfonic acid (0.38 g, 2 mmol) was refluxed in toluene (500 mL) for 15 hours with azeotropic removal of water. The solvent was removed in vacuo, and the residue redissolved in MeOH. The stirred solution was treated with solid sodium borohydride (1 g, 26.5 mmol) at room temperature for 1 hour. The solvent was removed in vacuo, the residue redissolved in methylene chloride, and extracted with 1N NaOH (aq) (2×100 mL), and water (2×100 mL). The dried (MgSO$_4$) organic phase was evaporated in vacuo and treated with etheral-hydrogen chloride$_{(g)}$ in methanol to afford the title compound (4.6 g, 9.0 mmol, 90% yield) as the dihydrochloride salt. The dihydrochloride salt was converted to the free base with 1N NaOH (aq) and extracted with methylene chloride. The organic phase was washed with water (2×75 mL), dried (MgSO$_4$), evaporated in vacuo, and the residue crystallized from ether-hexane to afford, after drying in vacuo (6 hours at 45° C.) overnight, the free base of the title compound, m.p. 72°–75° C.

$^1$H NMR (CDCl$_3$, 400 MHz) δ: 8.90 (d, J=4.4 Hz, 1H), 8.16 (dd, J=8.5, 0.6 Hz, 1H), 7.97 (ddd, J=8.3, 1.2, 0.6 Hz, 1H), 7.73 (ddd, J=8.3, 6.8, 1.5 Hz, 1H), 7.58 (ddd, J=8.3, 6.8, 1.3 Hz, 1H), 7.54 (d, J=4.6 Hz, 1H), 7.29 (m, 4H), 7.25 (d, J=8.7 Hz, 2H), 7.23 (m, 1H), 6.96 (d, J=8.5 Hz, 2H), 5.51 (s, 2H), 3.75 (s, 2H), 3.48 (s, 2H), 2.83 (dt, J=12.0, 2.7 Hz, 2H), 2.50 (m, 1H), 2.00 (td, J=11.4, 2.3 Hz, 2H), 1.87 (dd, J=13.7, 1.5 Hz, 2H), 1.44 (qd, J=11.6, 3.7 Hz, 2H)

MS (+FAB), m/z (rel. intensity)=4.38 (MH+, 20), 248 (20), 172 (20), 142 (50), 91 (100)

IR (KBr) v: 3430, 2930, 2800, 1595, 1580, 1510, 1360, 1250, 1230, 1100, 1065, 840, 760, 735, 690 cm$^{-1}$

Anal. Calcd. for $C_{29}H_{31}N_3O$: C, 79.60; H, 7.14; N, 9.60. Found: C, 79.57; H, 6.90; N, 9.57.

EXAMPLE 17

N-[1-(Phenylmethyl)-4-piperidinyl]-N-[[4-(4-quinolinylmethoxy)phenyl]methyl]butanamide Fifteen Hundredths Dichloromethane 1-(Phenylmethyl)-N-[[4-(4-quinolinylmethoxy)phenyl]methyl]-4-piperidinamine (1.31 g, 3 mmol) and butyric anhydride (0.79 g, 5 mmol) was stirred at room temperature for 7 hours in methylene chloride. After dilution with methylene chloride and extraction with 1N NaOH (aq) (2×100 mL), the organic phase was washed with water (3×100 mL), dried (MgSO$_4$), and evaporated to 1.2 g (2.4 mmol) of the title compound as a slightly amber oil in 79% yield.

$^1$H NMR (CDCl$_3$, 400 MHz, 2:1 mixture of rotomers) δ: 8.92 (d, J=4.4 Hz, 1H), 8.89 (d, J=4.4 Hz, 1H), 8.17 (d, J=8.4 Hz, 1H), 8.16 (d, J=8.3 Hz, 1H), 7.98 (d, J=8.3 Hz, 1H), 7.97 (d, J=8.3 Hz, 1H), 7.76 (m, 1H), 7.61 (m, 1H), 7.56 (d, J=4.4 Hz, 1H), 7.55 (d, J=4.4 Hz, 1H), 7.27 (m, 5H), 7.16 (d, J=8.6 Hz, 2H), 7.11 (d, J=8.6 Hz, 2H), 6.99 (d, J=8.6 Hz, 2H), 6.92 (d, J=8.6 Hz, 2H), 5.53 (s, 2H), 5.50 (s, 2H), 5.29 (s, 2H), 4.62 (m, 1H), 4.53 (s, 2H), 4.48 (s, 2H), 3.68 (m, 1H), 3.48 (s, 2H), 3.47 (s, 2H), 2.90 (m, 2H), 2.42 (t, J=7.4 Hz, 2H), 2.21 (t, J=7.3 Hz, 2H), 2.07 (m, 2H), 2.00 (t, J=12.7 Hz, 2H), 1.80 (q, J=12.1 Hz, 2H), 1.74 (sextet, J=7.5 Hz, 2H), 1.65 (sextet, J=7.4 Hz, 2H), 1.61 (m, 2H), 1.01 (t, J=7.4 Hz, 3H), 0.88 (t, J=7.4 Hz, 3H)

MS(CI), m/z (rel. intensity)=508 (MH+, 80), 335 (78), 264 (70), 170 (88), 144 (100)

IR (KBr) v: 3000, 2950, 1620, 1505, 1230, 840 cm$^{-1}$

Anal. Calcd. for $C_{33}H_{37}N_3O_2 \cdot 0.15\ CH_2Cl_2$: C, 76.51; H, 7.22; N, 8.07. Found: C, 76.38; H, 7.32; N, 8.07.

EXAMPLE 18

N-[1-(Phenylmethyl)-4-piperidinyl]-4-[(4-quinolinylmethyl)amino]benzamide

Step a) Preparation of 4-[(4-Quinolinylmethyl)amino]benzoic Acid

4-Quinolinecarboxaldehyde (10.0 g, 63.8 mmol) and methyl 4-aminobenzoate (9.64 g, 63.8 mmol) were refluxed under nitrogen in 100 mL of toluene with azeotropic removal of water. After 7 days, the reaction mixture was allowed to cool to room temperature. The imine precipitated as a yellow solid and was collected by filtration. The material was dried under reduced pressure overnight affording 15.5 g (53.4 mmol) of crude product. This was stirred in 270 mL of ethanol and treated with sodium borohydride (2.22 g, 58.7 mmol). The reaction mixture was refluxed for 45 minutes then poured hot over 800 mL of crushed ice. After 45 minutes of stirring, the white solid was filtered and allowed to air dry in the funnel overnight giving 15.6 g of 4-[(quinolinylmethyl)amino]benzoic acid as a 5:1 mixture of methyl:ethyl esters. All of the material was refluxed for 18 hours in 180 mL of 1N KOH and then poured hot into a mixture of 180 mL of 1N HCl and 800 mL of water. After 3 hours of stirring, the white solid was filtered and washed successively with methanol and ether affording 13.5 g (48.5 mmol, 76% overall yield) of 4-[(4-quinolinylmethyl)amino]benzoic acid which was air dried in the funnel overnight.

$^1$H NMR (Me$_2$SO-d$_6$, 300 MHz) δ: 12 (br s, 1H), 8.83 (d, J=4.4 Hz, 1H), 8.23 (d, J=8.3 Hz, 1H), 8.07 (d, J=8.5 Hz, 1H), 7.80 (t, J=7.6 Hz, 1H), 7.7 (m, 3H), 7.41 (d, J=4.4 Hz, 1H), 7.2 (br t, 1H), 6.63 (d, J=8.9 Hz, 2H), 4.49 (br d, J=5.9 Hz, 2H).

Step b) Preparation of N-[1-(Phenylmethyl)-4-piperidinyl]-4-[(4-quinolinylmethyl)amino]benzamide 1-(3-Dimethylaminopropyl)-3-ethylcarbodiimide hydrochloride (3.62 g, 18.9 mmol), 1-hydroxybenzotriazole hydrate (2.43 g, 18.0 mmol), and 4-[(4-quinolinylmethyl)amino]benzoic acid (5.00 g, 18.0 mmol) were placed in a flask under nitrogen. N,N-Dimethylformamide (83 mL) was then added followed by triethylamine (4.5 g, 45 mmol, 6.3 mL) and finally 4-amino-1-benzylpiperidine (3.1 g, 3.3 mL, 16 mmol). The mixture was heated at 100° C. for 45 minutes and the N,N-dimethylformamide was then removed under reduced pressure. The resulting viscous orange oil was triturated overnight with a mixture of 75 mL of water and 50 mL of ethyl acetate with vigorous overhead stirring. The resulting solid was filtered, washed with water and dried under reduced pressure at 60° C. for 25 hours. Flash chromatography on silica gel (65 mm column, 5% ammonia saturated methanol in methylene chloride eluent) afforded fractions containing the product which were concentrated to the point where a white powder formed. The powder was filtered and washed with a small amount of methanol and then ether. Drying under reduced pressure at 60° C. for 19.5 hours afforded 3.65 g (8.1 mmol, 50% yield) of the title compound, m.p. 184°–188° C.

$^1$H NMR (Me$_2$SO-d$_6$, 400 MHz) δ 8.8 (d, J=4.4 Hz, 1H), 8.23 (d, J=8.3 Hz, 1H), 8.05 (d, J=8.5 Hz, 1H) 7.6–7.8 (m, 5H), 7.2–7.4 (m, 6H), 6.91 (br t, J=5.9 Hz, 1H), 6.59 (d, J=8.8 Hz, 2H), 4.9 (d, J=5.7 Hz, 2H), 3.7 (m, 1H), 3.4 (s, 2H), 2.8 (m, 2H), 2 (m, 2H), 1.7 (m, 2H), 1.5 (m, 2H)

MS (EI), m/z (rel intensity)=450 (M+, 23), 307 (42), 278 (58), 261 (28), 189 (13) 172 (100)

IR (KBr) v: 3320, 3040, 2960, 1615 cm$^{-1}$

Anal. Calcd. for $C_{29}H_{30}N_4O$: C, 77.30; H, 6.71; N, 12.43. Found: C, 77.09; H, 6.73; N, 12.40.

EXAMPLE 19

N-(1-Butyl-4-piperidinyl)-4-[(4-quinolinylmethyl)amino]benzamide

The title compound was prepared from 4-[(4-quinolinylmethyl)amino]benzoic acid and 4-amino-1-butylpiperidine bishydrochloride by the procedure described in Example 18, m.p. 189°–190° C.

$^1$H NMR (Me$_2$SO-d$_6$, 400 MHz) δ: 8.8 (d, J=4.4. Hz, 1H), 8.2 (d, J=7.9 Hz, 1H), 8.05 (d, J=8.3 Hz, 1H), 7.6–7.8 (m, 5H), 7.4 (d, J=4.4 Hz, 1H), 6.91 (br t, J=5.9 Hz, 1H) 6.59 (d, J=8.9 Hz, 2H), 4.8 (d, J=5.8 Hz, 2H), 3.7 (m, 1H), 2.8 (m, 2H), 2.2 (m, 2H), 1.9 (m, 2H), 1.7 (m, 2H), 1.2–1.6 (m, 6H), 0.86 (t, J=7.3 Hz, 3H)

MS (EI), m/z (rel intensity)=416 (M+, 31), 373 (40), 261 (100)

IR (KBr) v: 3320, 3040, 2940, 1610 cm$^{-1}$

Anal. Calcd. for $C_{26}H_{32}N_4O$: C, 74.97; H, 7.74; N, 13.45. Found: C, 74.89; H, 7.68; N, 13.08.

The compounds of the present invention have potent activity as bradykinin inhibitors and as such possess therapeutic value as analgesics.

The following protocols describe assays for detecting bradykinin antagonists and bradykinin antagonist analgesics.

Protocol for Bradykinin Receptor Binding Assay

The purpose of this assay is to identify compounds which compete specifically with tritiated bradykinin ($^3$H—BK) for BK$_2$ receptor sites in guinea pig ileum.

The guinea pig (adult male Hartley strain, 350–500 g, Charles River) is euthanized by stunning followed by decapitation. The distal portion of the ileum is removed and placed in ice cold homogenization buffer (25 mM N-[tris(hydroxymethyl)methyl]-2-aminoethanesulfonic acid (TES), 1 mM 1,10-phenanthroline, adjusted to pH 6.8 with NH$_4$OH). The contents of the ileal lumen are rinsed out with cold homogenization buffer. The tissue is cut into small pieces and homogenized in 20 volumes of homogenization buffer.

The homogenate is filtered through a surgical gauze sponge and centrifuged at 50,000×g for 20 minutes at 4° C. The supernatant fluid is discarded and the homogenization and centrifugation procedure is repeated. After discarding the supernatant fluid, the final pellet is resuspended in 40 volumes of assay buffer (25 mM TES, pH=6.8, 1 mM 1,10-phenanthroline, 1 mM (2RS, 3RS)-1,4-dimercapto-2,3-butanediol (Cleland's reagent), 2 μM captopril, 140 μg/mL bacitracin and 0.1% bovine serum albumin (BSA)). The homogenate is filtered once more through a surgical gauze sponge and kept on ice until use.

The assay is performed using only polypropylene pipet tips and polypropylene test tubes. Each tube receives 100 μL of 800 pM $^3$H—BK, 100 μL of the test compound solution or vehicle (TES assay buffer), and 100 μL of 25 mg/mL tissue homogenate in a total volume of 1 mL. The final concentration of $^3$H—BK is 80 pM. The final tissue concentration is 2.5 mg/mL. Compounds are screened at 100 μM or 10 μM. Nonspecific binding is determined in the presence of 1 μM unlabeled bradykinin. All determinations are made in triplicate. Three 100 μL aliquots of the 800 pM $^3$H—BK working solution are added directly to scintillation vials to determine the total added radioactivity.

The tubes are incubated for 90 minutes at 25° C. while being gently agitated on an orbital shaker. Bound ligand is separated from free ligand, using Whatman GF/B glass fiber filters (pretreated with 0.1% aqueous polyethyleneimine made neutral with HCl). Assay tubes and glass fiber filters are rinsed three times with 3 mL of cold physiological saline.

The filter discs are transferred to 20 mL scintillation vials. Ten mL of aqueous sample LSC cocktail (Aquassure, New England Nuclear) is added to each vial. After capping, the vials are agitated for 5 minutes on an orbital shaker. The samples are counted for ten minutes in a refrigerated liquid scintillation counter.

The following values are obtained:
$B_t$: Total binding
$B_{ns}$: Nonspecific binding
$B_x$: Total binding in the presence of the test compound
C: Control specific binding $C = B_t - B_{ns}$
D: Specific binding in the presence of the test compound $D = B_x - B_{ns}$
Percent of Control: $D/C \times 100$
Percent Inhibition: $(1 - D/C) \times 100$ After calculation of Percent of Control for each dilution, the values are analyzed and the IC$_{50}$ with its 95% confidence limits is determined on a Hewlett Packard 9816 computer using the program "PS-NONLIN" (generalized non-linear regression with inverse prediction and graphics).

The test results are reported in the TABLE below under the heading 3H—BK Binding, G. P. Ileum.

Protocol for Bradykinin-induced Writhing in Mice

The purpose of this assay is to determine the ability of test drugs to inhibit the writhing response induced by bradykinin in mice. This test is a primary in vivo screen for bradykinin antagonist analgesics.

Groups of 10 mice each (male CD-1 mice (14-19 g) from Charles River, Kingston, NY, fasted overnight prior to experiment, but having free access to water) are used. Each mouse receives an intraperitoneal injection of 1 mg/kg PGE$_2$ (0.1 mL/10 g body weight) followed 20 minutes later by an i.p. injection of bradykinin 0.5 mg/kg. The number of writhes per mouse is determined for 2 minutes after bradykinin injection. For a primary screen, drugs are administered orally at 20 mg/kg 1 hour prior to the bradykinin.

The percent inhibition of writhing obtained is calculated as follows:

$$100 \times \frac{C-D}{C}$$

Several logarithmically spaced doses are tested and the ED$_{50}$ (dose which inhibits the writhing response by 50%) is determined by regression methods with inverse prediction.

The test results are reported in the TABLE below under the heading BK Induced Writhing in Mice.

Protocol for Bradykinin-induced Hyperalgesia in Rats

The purpose of this assay is to evaluate analgesic activity of bradykinin antagonists in an inflammatory pain model in rats.

Animals (female Sprague Dawley rats (Charles River, Kingston, NY) 80-115 gms) are fasted overnight, with water given ad lib, if the compounds are to be administered orally. Ten rats are used per test group and six per normal group.

Test compounds are suspended in 0.5% Tween 80 in distilled water, and are administered orally 1 hour (or i.p. 5 minutes) prior to the injection of bradykinin.

The animals are randomized prior to drug administration in order to make the study blind. Bradykinin is injected, as the phlogistic agent, into the subplantar region of the right hindpaw of the rats, in a 0.01 mg/0.1 mL saline solution. The pain threshold is measured 1 minute later using a modification of the Randall-Selitto method, [Randall, et al., Archives International Pharmacodynamics, VIII N4, p 409-419 (1957)].

Animals are placed in a horizontal position with a hindpaw hanging down on the apparatus. The teflon point is placed on the foot pad and a steady pressure is applied, using a foot pedal. The endpoint is determined when the rat emits a squeak or forcefully attempts to remove its paw from the apparatus. Both paws of each animal are tested in this manner, the left paw serving as a normal control.

Drug effects are expressed as a percent change in pain threshold from bradykinin control values.

The ED$_{50}$ and 95% C.L. (dose which increases the pain threshold of the inflamed paw in drug groups by 50% relative to the control group) are determined by linear regression.

TABLE

| Example | 3H-BK Binding, G.P. Ileum | | BK Induced Writhing in Mice | |
|---|---|---|---|---|
| | % inhibition at 100 μM (10 μM) | IC$_{50}$ (μM) | % inhibition at 30 mg/kg i.p. | ED$_{50}$ (mg/kg) |
| 1* *44.8% increase of BK induced pain threshold in rats at 100 mg/kg p.o. | 98.8 | 9.1 | 40.0 @ 30 mg/kg i.p. 52.0 @ 300 mg/kg p.o. | 332.0 (p.o.) |
| 2 | 93.8 | 33.6 | 40.0 @ 30 mg/kg i.p. 32.0 @ 100 mg/kg p.o. 22.5 @ 200 mg/kg p.o. | |

TABLE-continued

| | 3H-BK Binding, G.P. Ileum | | BK Induced Writhing in Mice | |
| --- | --- | --- | --- | --- |
| Example | % inhibition at 100 μM (10 μM) | IC$_{50}$ (μM) | % inhibition at 30 mg/kg i.p. | ED$_{50}$ (mg/kg) |
| 3 | 15.2 (10 μM) | | | |
| 4 | 10.4 (10 μM) | | | |
| 5 | 63.8 (10 μM) | 7.3 | 31.0 @ 30 mg/kg i.p. 22.0 @ 200 mg/kg p.o. | |
| 6 | 17.3 (10 μM) | | | |
| 7 | 43.2 (10 μM) | | | |
| 8 | 8.4 (10 μM) | | | |
| 9 | 21.4 (10 μM) | | | |
| 10 | 8.6 (10 μM) | | | |
| 11 | 11.1 (10 μM) | | | |
| 12 | 78.7 (10 μM) | | 10.0 | |
| 13 | 35.8 (10 μM) | | | |
| 14 | 30.2 (10 μM) | | | |
| 15 | 30.2 (10 μM) | | | |
| 16 | 27.4 (10 μM) | | | |
| 17 | 25.3 (10 μM) | | | |
| 18 | 8.1 (10 μM) | | | |
| 19 | 32.8 (10 μM) | | | |

We claim:

1. A method for the treatment of pain in mammals which comprises administering orally or parenterally thereto, in therapeutically effective analgesic doses, at least one compound of the formula

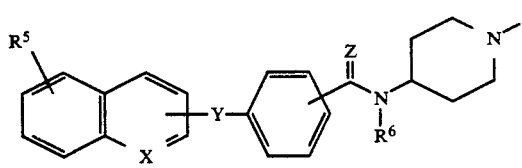

wherein X is nitrogen, NO or CR$^1$; Y is C(R$^1$)(R$^2$)O, OC(R$^1$)(R$^2$), C(R$^1$)(R$^2$)N(R$^3$), N(R$^3$)C(R$^1$)(R$^2$) or C(R$^1$)=C(R$^2$); wherein R$^1$, R$^2$, and R$^3$ are independently hydrogen or lower alkyl containing 1 to 10 carbon atoms; Z is oxygen or (R$^1$)(R$^2$); R$^4$ is R$^1$, benzyl, benzyl ring substituted with R$^5$, benzyl alpha monosubstituted with R$^1$, benzyl ring substituted with R$^5$ and alpha monosubstituted with R$^1$, phenyl, phenylalkyl containing 2 to 10 carbon atoms in the alkyl group or phenylalkyl ring substituted with R$^5$ and containing 2 to 10 carbon atoms in the alkyl group; wherein R$^5$ is R$^1$, lower alkoxy containing 1 to 10 carbon atoms, halogen, trihalomethyl, NO$_2$, N(R$^1$)(R$^2$) or C(O)N(R$^1$)(R$^2$); R$^6$ is R$^1$ or R$^6$ is C(O)(R$^7$) with the proviso that Z is not oxygen; and wherein R$^7$ is R$^1$, phenyl, perfluoroalkyl containing 1 to 10 carbon atoms, phenylalkyl containing 1 to 10 carbon atoms in the alkyl group or a pharmaceutically acceptable acid addition salt thereof.

* * * * *